United States Patent [19]

Caruthers et al.

[11] Patent Number: 4,716,217

[45] Date of Patent: Dec. 29, 1987

[54] HYBRID LYMPHOBLASTOID-LEUKOCYTE HUMAN INTERFERONS

[75] Inventors: Marvin H. Caruthers, Boulder, Colo.; Michael Leineweber, Frankfurt am Main, Fed. Rep. of Germany; Moshe Leitner, Rehovot, Israel; Yitzhak Stabinsky, Boulder, Colo.

[73] Assignee: University Patents, Inc., Westport, Conn.

[21] Appl. No.: 646,866

[22] Filed: Aug. 31, 1984

[51] Int. Cl.[4] .................... C07K 13/00; C07K 15/26; A61K 45/02
[52] U.S. Cl. .................................... 530/351; 424/85; 435/68; 435/811
[58] Field of Search ................... 530/351; 424/85; 435/68, 811, 172.3

[56] References Cited

U.S. PATENT DOCUMENTS 4,414,150  11/1983  Goeddel ............................ 424/85
4,569,908   2/1986  Mark et al. ....................... 435/811

OTHER PUBLICATIONS

Shepard et al., Nature, vol. 294, pp. 563–565, 1981.

*Primary Examiner*—Blondel Hazel
*Attorney, Agent, or Firm*—Thomas J. Monahan

[57] ABSTRACT

DNA sequences encoding for novel human lymphoblastoid-leukocyte hybrid interferons. Methods of making nucleotide sequences comprising ribosome binding sites, promoter regions, and segments of human lymphoblastoid and leukocyte interferons are described. DNA sequences for hybrid interferons are cloned and expressed in plasmid vectors. Transformed microorganisms and novel lymphoblastoid-leukocyte polypeptide interferons having biological or immunological activity are disclosed.

8 Claims, 3 Drawing Figures

HYBRID LYMPHOBLASTOID-LEUKOCYTE HUMAN INTERFERONS

The invention herein described relates to a method for the construction of a nucleotide sequence encoding for novel hybrid lymphoblastoid-leukocyte human interferons and including a hybrid promoter and ribosome binding sites useful for the expression of the hybrid interferons. The synthetic DNA sequences are introduced into plasmid vectors and subsequently introduced into microorganisms. Transformed microorganisms and the expression of novel hybrid interferons are described.

By way of background, it is well known that there are numerous commercial applications of microorganisms. For example, both eukaryotic and prokaryotic microorganisms have long been used for the treatment of wastes, as sources of protein and medicinal products, and for diverse biological conversions into both primary and secondary metabolites [Sci. Amer. 245: 67–74 (1981)]. More recently, it has become possible to transfer operative genes among microorganisms and between microorganisms and various higher forms of life. The modern techniques of genetic engineering, with particular reference to recombinant DNA/RNA technology, now makes it theoreticaly possible to transfer any gene or group of genes to a plasmid capable of functioning in microorganisms.

Genetic recombination is the biological process whereby genetic information is exchanged between chromosomes. The fields of both classical and molecular genetics involve resolution of the complexities of genetic recombination. Recombination ordinarily does not occur between unrelated species of organisms. Nevertheless, the new recombinant DNA technologies now allow the transfer of genes between related or unrelated organisms [Amer. Sci., 68: 664–674 (1980)]. The genetic alteration of gene structure has particular application in the field of industrial microbiology [Sci. Amer. 245: 91–102 (1981)].

Genetic recombination involves the breaking and splicing of molecules of DNA. It is now possible to gather diverse genetic information in vitro in the form of DNA fragments from various prokaryotic and eukaryotic sources and to introduce this genetic material into a self-replicating genetic moiety known as a cloning vector. DNA fragments, or even intact genes, can be constructed by synthetic chemical means to correspond to desired theoretical genetic sequences, or to known genetic sequences, and then introduced into a selected vector. Cloning vectors are commonly bacterial plasmids or bacteriophages. Plasmids are autonomous extrachromosomal genetic units which consist of a circular strand of DNA and are present in most bacteria and in some eukaryotes. Bacteriophages are DNA viruses which parasitize only bacteria. The hybrid genetic vectors are then introduced into selected microorganisms in a process known as transformation. Thus transformed microorganisms are potential factories useful for the production of large amounts of the cloned DNA.

The foreign genetic information present in the cloning vector is often not expressed in the transformed microorganisms. A non-expressing cloning vector may be desirable in those instances where expression of the foreign genome could produce a product lethal to the host organism. A non-expressing or low-expressing cloning vector represents a ready source of the foreign genetic material which can then be isolated in vitro and introduced into an expression vector (i.e., a specially prepared or selected plasmid). The foreign DNA is placed in a suitable location (i.e., inserted within the lac operon) in an expression vector where the indigenous genetic sequence is such that the foreign genetic information will be transcribed (i.e., mRNA produced from the foreign DNA) and translated (i.e., protein synthesis from the mRNA template) and the desired product (coded in the foreign DNA) obtained. As with the manufacture of the cloning vector, the expression vector introduced into a selected microorganism and the resultant transformed microbe serve as a factory for the manufacture of the foreign-DNA product.

With the development of the class of enzymes known as restriction endonucleases, DNA can now be cut in vitro at specific locations in preparation for insertion into an appropriate transfer vector. Restriction endonucleases are enzymes which are site-specific endonucleases which primarily cleave double-stranded DNA but in some instances cleave single-stranded DNA. All restriction endonucleases recognize specific DNA sequences. Class II restriction endonucleases cleave at specific sequences, whereas Class I restriction endonucleases appear to cleave DNA randomly and produce heterogeneous products. Various restriction endonucleases produce DNA fragments of different lengths and types. For example, some restriction endonucleases cleave both DNA strands at the same point and produce "blunt end" DNA fragments, in contrast to other enzymes which cleave one DNA strand several nucleotides away from the cleavage on the complementary strand and produce "cohesive end" DNA fragments. A practitioner in the recombinant DNA art by creative selection of endonucleases for treatment of subject DNA can obtain desired DNA fragments which can then be joined together by the action of a DNA ligase. In this manner the cutting and splicing of genetic information (DNA) is accomplished. Following the insertion of foreign DNA into a microbe, the exact sequences which have been cloned can be determined by DNA sequencing procedures.

In order to effect a desired end sequence of subject DNA fragments (i.e., for ligation purposes), nucelotides can be added to the terminal portion of such DNA. For example, in the process known as homopolymeric tailing, a series of identicl deoxyribonucleotides is added to the 3' ends of the cloning vector and a series of complementary deoxyribonucleotides is added to the 3' ends of the DNA fragments to be cloned. These DNA sequences can then be joined and introduced into a microbial host.

Another general method for obtaining a desired DNA fusion product is the addition of "adapter" or "linker fragments" to the ends of either or both the cloning vector or the DNA fragments to be cloned. Linker fragments are small sections of DNA that contain one or more recognition sequences for restriction endonucleases.

Following the insertion of foreign DNA into a microbe, the exact sequences which have been cloned can be determined by DNA sequencing procedures.

There are several ways in which foreign DNA material can be obtained for insertion into a transfer vector. DNA fragments directly obtained from the parental source can be inserted into the appropriate vector. Another method is to obtain mRNA from an active synthesis location (product expression area) in the parent system and to obtain a single-stranded complementary DNA strand synthesized enzymatically (reverse transcriptase) from the isolated mRNA. A double-stranded DNA molecule is then synthesized from the single stranded template. Double-stranded DNA obtained in this fashion is known as complementary DNA (cDNA). Once a desired DNA sequence is known, genes can also be chemically synthesized in vitro for cloning/expression purposes in microbial, tissue, or cell culture systems.

Interferons are a large family of proteins released by various animal cells exposed to a virus which enable other cells to resist infection. Interferons vary from species to species. Although their mode of action is not yet well understood, they are generally believed to be antiviral in nature. Presumably, interferons may be effective against viral diseases and perhaps cancers. Interferon is known to have various biological activities other than those which contribute to antiviral effects. Three classes or groups of human interferons have been identified: alpha or leukocyte interferon; beta or fibroblast interferon; and gamma or immune interferon.

Alpha or leukocyte interferons are a family of related proteins having a chain length consisting of 165 or 166 amino acids. At least eight distant subtypes of alpha interferon have been detected by cloning cDNAs from leukocyte mRNAs. Many different alpha interferons have already been isolated and characterized. By use of recombinant DNA technology, it is now possible to isolate and characterize human interferon genes and to clone them into bacteria or other microorganisms for the production of quantitatively significant amounts of interferons for experimental and medical purposes.

Lymphocytes are white blood cells (leukocytes) formed in lymphoid tissue, and lymphoblasts are immature lymphocytes. The chemical sequence of several human leukocyte interferons is known. However, the amino acid sequences of certain lymphoblastoid interferons have not yet been completely characterized. Among these partially characterized interferons is the lymphoblastoid interferon produced by the induction of Namalva cells with Newcastle disease virus, strain B1 [Proc. Natl. Acad. Sci., 76: 5601-5605 (1979); J. Biol. Chem., 252: 6585-6587 (1977)]. A portion of the amino acid sequence of this protein has been determined but the entire sequence is not among the known α-interferons. This lymphoblastoid interferon is an attractive candidate for gene synthesis for several reasons. Firstly, the interferon is expressed naturally as the result of a viral infection in sufficient quantities for isolation and various biological and biochemical studies. Secondly, the gene for this interferon is not among known cloned interferon genes. Lastly, lymphoblastoid interferons which occur naturally are among the major classes of interferons currently undergoing clinical trials for medical purposes.

The characterization, purification and manufacture of interferons using recombinant DNA procedures has been reviewed [Sci. Amer. 249: 37-43 (1983)]. Various hybrid human leukocyte interferons are described in U.S. Pat. No. 4,414,150. In addition, gene sequences, recombinant DNA molecules, transformed microorganisms, and methods for producing human interferon-like polypeptides are described in European Patent Application No. 32,134.

In light of the foregoing discussion of some of the recent advances in the field of genetic engineering, and more specifically to the identification, chemical characterization and manufacture of human interferons, an improved method for the preparation of novel interferon genes is highly desirable. An object of this invention is to produce novel hybrid human interferons comprising polypeptide sections of lymphoblastoid interferon and leukocyte interferon. Another object of this invention is to synthesize the eucaryotic gene sequence coding for novel lymphoblastoid-leukocyte hybrid proteins, including the synthesis of a gene section coding for appropriate ribosome binding sites and a promoter region. Yet another object of this invention is to clone synthesized hybrid lymphoblastoid-leukocyte gene sequences in an appropriate vector and microbial system and to subsequently gain expression of novel hybrid interferons having biological activity. Yet another object of this invention is to develop novel transformed microorganisms containing the nucleotide sequence encoding for novel lymphoblastoid-leukocyte hybrid interferons useful as antiviral agents. These and further objects are manifest in the following description and particularly delineated in the appended claims.

The accompanying drawings, which are incorporated in and constitute part of the specification, illustrate embodiments of the invention, and together with the description, serve to explain the principles of the invention.

Figure 1:
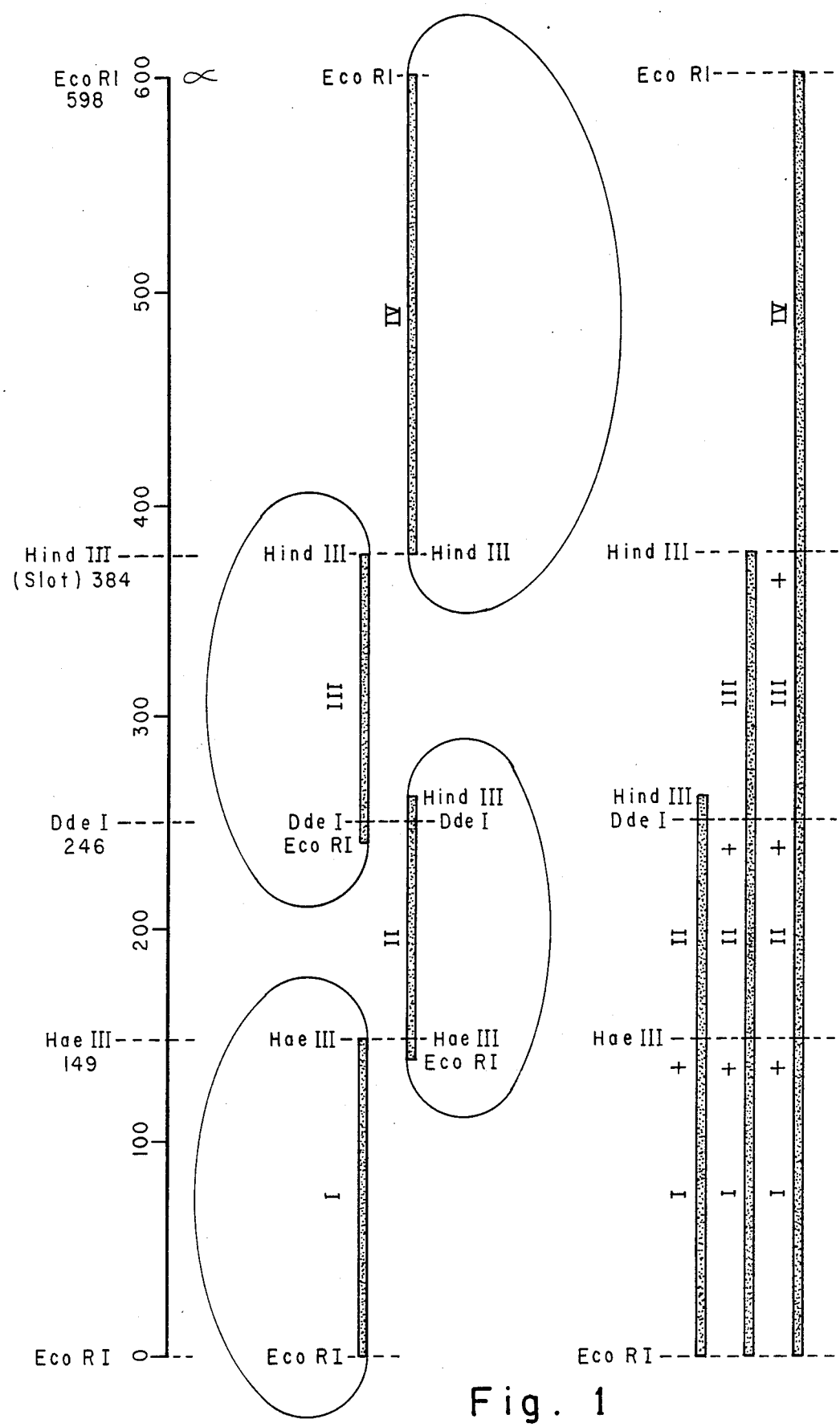
FIG. 1: A schematic outline of the interferon gene with the key restriction sites, including the four sections as cloned in plasmids and the plan for stepwise joining these sections is presented.

The synthesis of a gene containing certain lymphoblastoid interferons and leukocyte interferon sequences is described. Embodiments comprise either alpha C, F, or I-type leukocyte interferon sequences. The synthesis method is designed so that lymphoblastoid interferon sequences can be combined with either alpha C, F, or I leukocyte interferon sequences. The method of synthesis of the hybrid interferon gene sequences of the invention involves a combination of chemical and enzymatic procedures. In addition, the derivation of a hybrid promoter and three hybrid ribosome binding sites useful for the expression of this gene is described.

The lymphoblastoid hybrid interferon gene is composed of a 598 base pair DNA duplex. The gene sequence codes for the 166 amino acids of the structural gene, an intiation codon, two termination codons and a control region containing a promoter, an operator and a ribosome binding site. The DNA base-paired sequence for this gene, together with the amino acids for which it is coded, is presented in Table 1. Directly above the DNA sequence are numbers every 20 base pairs that designate nucleotides relative to the 5= EcoRI cut site on the sense strand which is number 1. Above the numbers are brackets which define the lambda $P_R$/T7 A2 promoter, lac operator, R1 ribosome binding site, and the structural gene. The brackets defining R1 extend through the eighth amino acid codon. The amino acid sequence for the lymphoblastoid hybrid gene is located above the appropriate codons of the DNA sense strand. Near the 3' end of the sense strand can be found two termination codons and at the 3' terminum, the EcoRI 3' cut site. Also shown by underlining are certain key restriction sites: EcoRI (twice), AluI, HaeIII, DdeI, and ribosome binding site, and protein coding region are hybrid structures and do not correspond to any known natural DNA sequences.

TABLE 1
Lymphoblastoid Hydbrid Interferon Gene Sequence

```
                                                                              Lambda P_R/T7 AZ—
  Eco RI                                                 20
5'-A—A—T—T—C—A—C—C—G—Ṫ—G—C—G—T—G—T—T—G—A—Ċ—T—A—T—T—T—T—A—C—C—Ṫ—
3'-          G—T—G—G—C—A—C—G—C—A—C—A—A—C—T—G—A—T—A—A—A—A—T—G—G—A—
  operator───────────────┤├────────────────────────── Ribosome Binding Site ──────────

┤├──────────────────── Lac
                     40                                                        60
—C—T—G—G—C—G—G—T—G—Ȧ—T—A—A—T—G—A—A—A—T—Ċ—A—A—T—T—G—T—G—A—G—Ċ—
—G—A—C—C—G—C—C—A—C—T—A—T—T—A—C—T—T—T—A—G—T—T—A—A—C—A—C—T—C—G—
                                                                  ┘

80
Ġ—G—A—T—A—A—C—A—A—Ṫ—T—A—A—A—A—A—T—A—Ȧ—G—G—A—G—G—A—T—C—A—Ċ—
C—C—T—A—T—T—G—T—T—A—A—T—T—T—T—T—A—A—T—T—C—C—T—C—C—T—A—G—T—G— met           cys           asp           leu           pro           gln           thr           his           ser           leu
                                                 100                                                              AluI          120
—T—A—T—G—T—G—T—G—A—Ṫ—T—T—G—C—C—G—C—A—G—Ȧ—C—T—C—A—T—A—G—C—T—Ṫ—
—A—T—A—C—A—C—A—C—T—A—A—A—C—G—G—C—G—T—C—T—G—A—G—T—A—T—C—G—A—A— gly           asn           arg           arg           ala           leu           ileu          leu           leu           ala
                                                                                         140                                    Hae III
—G—G—G—C—A—A—C—C—G—Ȧ—A—G—A—G—C—A—C—T—C—Ȧ—T—C—C—T—G—T—T—G—G—Ċ—C—
—C—C—C—G—T—T—G—G—C—T—T—C—T—C—G—T—G—A—G—T—A—G—G—A—C—A—A—C—C—G—G— gln           met           gly           arg           ileu          ser           leu           phe           ser           cys
                                     160                                                                                         180
—C—A—A—A—T—G—G—G—Ṫ—C—G—C—A—T—T—T—C—C—Ċ—T—G—T—T—C—T—C—G—T—Ġ—
—G—T—T—T—A—C—C—C—A—G—C—G—T—A—A—A—G—G—G—A—C—A—A—G—A—G—C—A—C—

HindIII. The major elements of this gene-promoter, leu           lys           asp           arg           his           asp           phe           gly           phe           pro
                                                                  200
—C—C—T—T—A—A—A—G—A—Ċ—C—G—C—C—A—C—G—A—T—Ṫ—T—C—G—G—G—T—T—T—C—Ċ—
—G—G—A—A—T—T—T—C—T—G—G—C—G—G—T—G—C—T—A—A—A—G—C—C—C—A—A—A—G—G— gln           glu           glu           phe           asp           gly           asn           gln           phe           gln
                                                 220                                                                              240
—A—C—A—G—G—A—A—G—A—Ġ—T—T—T—G—A—C—G—G—C—Ȧ—A—T—C—A—G—T—T—C—C—Ȧ—
—T—G—T—C—C—T—T—C—T—C—A—A—A—C—T—G—C—C—G—T—T—A—G—T—C—A—A—G—G—T— lys           ala           gln           ala           ileu          ser           val           leu           his           glu
                     DdeI                                                   260
—A—A—A—G—G—C—T—C—A—Ġ—G—C—A—A—T—C—T—C—G—Ġ—T—T—C—T—G—C—A—T—G—Ȧ—
—T—T—T—C—C—G—A—G—T—C—C—G—T—T—A—G—A—G—C—C—A—A—G—A—C—G—T—A—C—T— met           ileu          gln           gln           ileu          phe           asn           leu           phe           ser
                                     280                                                                                         300
—G—A—T—G—A—T—T—C—A—Ġ—C—A—A—A—T—C—T—T—C—Ȧ—A—C—C—T—G—T—T—C—T—Ċ—
—C—T—A—C—T—A—A—G—T—C—G—T—T—T—A—G—A—A—G—T—T—G—G—A—C—A—A—G—A—G— thr           lys           asp           ser           ser           ala           ala           trp           asn           glu
                                                                  320
—C—A—C—T—A—A—A—G—A—Ċ—T—C—T—T—C—G—G—C—T—Ġ—C—T—T—G—G—A—A—C—G—Ȧ—
—G—T—G—A—T—T—T—C—T—G—A—G—A—A—G—C—C—G—A—C—G—A—A—C—C—T—T—G—C—T— ser           leu           leu           asp           lys           phe           ser           thr           glu           leu
                                                 340                                                                              360
—A—T—C—C—T—T—G—C—T—Ṫ—G—A—T—A—A—A—T—T—C—Ṫ—C—C—A—C—T—G—A—A—C—Ṫ—
—T—A—G—G—A—A—C—G—A—A—C—T—A—T—T—T—A—A—G—A—G—G—T—G—A—C—T—T—G—A—
```

-continued

```
—tyr————gln————gln————leu————asn————asp————leu————glu————ala————cys————
                                                    380              Hind III
—C—T—A—T—C—A—G—C—A—Ȧ—C—T—G—A—A—C—G—A—T—Ċ—T—T—G—A—A—G—C—T—T—G—
—G—A—T—A—G—T—C—G—T—T—G—A—C—T—T—G—C—T—A—G—A—A—C—T—T—C—G—A—A—C—

—val————ileu————gln————glu————val————gly————val————glu————glu————thr————
              400                                                       420
—C—G—T—T—A—T—C—C—A—Ġ—G—A—G—G—T—A—G—G—C—Ġ—T—T—G—A—A—G—A—G—A—Ċ—
—G—C—A—A—T—A—G—G—T—C—C—T—C—C—A—T—C—C—G—C—A—A—C—T—T—C—T—C—T—G—

—pro————leu————met————asn————val————glu————ser————ileu————leu————ala————
                                                  440
—T—C—C—G—C—T—T—A—T—Ġ—A—A—T—G—T—T—G—A—G—Ṫ—C—T—A—T—C—C—T—G—G—Ċ—
—A—G—G—C—G—A—A—T—A—C—T—T—A—C—A—A—C—T—C—A—G—A—T—A—G—G—A—C—C—G—

—val————ser————lys————tyr————phe————gln————arg————ileu————thr————leu————
              460                                                       480
—T—G—T—A—T—C—T—A—A—Ġ—T—A—T—T—T—T—C—A—G—Ċ—G—A—A—T—T—A—C—C—C—Ṫ—
—A—C—A—T—A—G—A—T—T—C—A—T—A—A—A—A—G—T—C—G—C—T—T—A—A—T—G—G—G—A—

—tyr————leu————ser————glu————lys————lys————tyr————ser————pro————cys————
                                        500
—C—T—A—C—C—T—C—A—G—Ṫ—G—A—G—A—A—G—A—A—A—Ṫ—A—T—T—C—A—C—C—G—T—Ġ—
—G—A—T—G—G—A—G—T—C—A—C—T—C—T—T—C—T—T—T—A—T—A—A—G—T—G—G—C—A—C—

—ala————trp————glu————ileu————val————arg————ala————glu————ileu————met————
              520                                                       540
—T—G—C—G—T—G—G—A—Ȧ—A—T—T—G—T—G—A—G—A—Ġ—C—C—G—A—A—A—T—C—A—Ṫ—
—A—C—G—C—A—C—C—T—T—T—A—A—C—A—C—T—C—T—C—G—G—C—T—T—T—A—G—T—A—

—arg————ser————leu————thr————leu————leu————thr————asn————leu————gln————
                                              560
—G—C—G—T—T—C—C—C̲—T—Ġ—A—C—T—C—T—T—C—T—G—Ȧ—C—G—A—A—C—C—T—C—C—Ȧ—
—C—G—C—A—A—G—G—A—C—T—G—A—G—A—A—G—A—C—T—G—C—T—T—G—G—A—G—G—T—

—glu————arg————leu————arg————asn————lys————asp————term————term————
              580                                           600
—G—G—A—A—C—G—C—C—T—Ġ—C—G—T—A—A—T—A—A—A—Ġ—A—C—T—A—A—T—A—G—         .Eco RI
—C—C—T—T—G—C—G—G—A—C—G—C—A—T—T—A—T—T—T—C—T—G—A—T—T—A—T—C—T̲—T̲—A̲—A̲
```

The promoter (1-71) is primarily the lambda major rightward promoter (lambda P$_R$) and the lac operator. The objective was to design a transcriptionally very active promoter under lac control. At the time this project was initiated, no such promoter was known. However, a combination of the tryptophan operon promoter with the lac operator was independently developed at about the same time (the lac promoter) and these two constructions were published simultaneously [Caruthers, M. H., et al., In Promoters, Structure and Function (R. Rodriguez and M. Chamberlin, eds.), Praeger, N.Y., 1982, pp. 432-451; DeBoer, H. A., et al., In Promoters, Structure and Function (R. Rodriguez and M. Chamerlin, eds.), Praeger, N.Y., 1982, pp. 462-481]. Additionally, the specific selection of a hybrid promoter containing lambda P$_R$ in combination with lac operator was especially attractive as a model system for independent studies on protein-DNA interaction mechanisms. This particular hybrid promoter would be recognized by E. coli RNA polymerase, lac repressor, cro repressor, and cI repressor. The interactions of these various proteins with the same DNA (modified or unmodified) could therefore be studied. Lambda P$_R$ was specifically selected in contrast to lambda P$_L$ because it could be extended to include the lambda P$_{RM}$ promoter. Once extended to contain two promoters, the DNA could be used to study promoter selection by E. coli RNA polymerase as a function of sequence modification. An early construction of the hybrid lambda P$_R$/T7 A2/lac promoter was simply the lac operator sequence (position 51-71) combined with the lambda P$_R$ promoter sequence (not shown) between 6-50. However, a lambda P$_R$ sequence (dAATGGT) between the −10 region and the transcription initiation site was homologous with the lac operator sequence from 51-56 (dAATTGT). The homology created difficulties when T4 DNA ligase was used in attempts to join synthetic oligodeoxynucleotides located in this region of the gene. The homology was eliminated by changing nucleotides 46-49 to the sequence found at these positions (relative to transcription initiation) in the T7 A2 promoter. Such a substitution was not considered detrimental to transcription activity of the hybrid promoter since among promoters the sequence in this region is highly variable. Therefore the final promoter DNA sequence is a composite of the lambda P$_R$ (5-45), T7 A2 (46-50) and lac (51-71) promoters. The transcription activity of this hybrid promoter was compared to the activity of the lac promoter. Both promoters were cloned into the same plasmid background and assayed for β-galactosidase activity in a lac deletion strain of E. coli. The lambda P$_R$/T7 A2/lac hybrid promoter is found to be approximately 50% more active than the fully induced lac promoter and approximately fourfold more active than the lac promoter under catabolite repression (glucose as the carbon source).

Ribosome binding sites still remain as undefined structures. Clearly translation from a ribosome binding site in *E. coli* starts from either an AUG or a GUG codon which is usually located approximately 6-8 nucleotides from a purine-rich DNA segment called the Shine and Dalgarno sequence. Based on systematic comparisons of a large number of ribosome binding sites, several additional observations on important sequence elements within these sites have been postulated [Scherer, G., et al. Nucleic Acids Res. 8: 3895-3907 (1980)]. Table 2 presents these different ribosome binding sites. The first eight amino terminal amino acids coded by the lymphoblastoid hybrid interferon gene of the invention are shown. The clustered set of partial ribosome binding sites that will code for this protein sequence is shown direcly below these amino acids. Also shown are ribosome binding sites R1, R2, and R3 and the idealized or known ribosome binding sites (R.B.S.) from which they were developed.

ing site sequence between 86-90. R1 as shown in Table 2 therefore contained wherever possible nucleotides corresponding to the model sequence. Modifications were however introduced to include the correct codons for the lymphoblastoid interferon gene, to position the AUG codon in the loop portion of the hair-pin structure, and to locate the Shine and Dalgarno sequence in a single stranded region 5' to the base paired stem structure. Ribosome binding sites R2 and R3 were derived differently by modification of known ribosome binding sites. Early research by J. Steitz using translation initiation complexes demonstrated that approximately 40 ribonucleotides of mRNA centered on the AUG codon were protected from nuclease digestion by ribosomes [Nature New Biol. 236: 71-75 (1972)]. This protected sequence is now generally defined as the ribosome binding site. The 20 or so nucleotides located 3' to the AUG initiation codon are quite variable and dependent on the amino terminal amino acid sequence of a particular protein. The first step in deriving the nucleotide sequences of R2 and R3 was to identify known ribosome binding sites with potential homology to the lymphoblastoid interferon amino acid sequence. This was accomplished TABLE 2
Ribosome Binding Sites Amino Acid Sequence: met——cys——asp——leu——pro——gln——thr——his——

Amino Acid Codons: A U G U G$_G^U$ G A C$_C^U$ U$_C^U$ C C$_C^U$ U$_C^U$ C A$_G^A$ A C$_C^U$ C A$_C^U$
(with A above pro codon and A above thr codon, G below under pro and thr)

Derived R1 Sequence
A A A A A U U A A G G A G G A U C A C U A U G U G U G A U U U G C C G C A G A C U C A U Idealized Sequence
a a a a a u u a a g g a g g a u c a c u a u g u g u g a u u u g c c g c a g a c u c a u Derived R2 Sequence
A U U A C C C A A C U U G A G G A A U U U A U A A U G U G U G A U U U A C C A C A A A C C A U L11 R. B. S. Sequence
a u u a c c c a a c u u g a g g a a u u u a u a a u g u g u g a u u u a c c a c a a a c c a u Derived R3 Sequence
C G G C C C C U U A C U U G A G G A U A A A U U A U G U G U G A U C U U C C A C A A A C C C A U φXF R. B. S. Sequence
c g g c c c c u u a c u u g a g g a u a a a u u a u g u g u g a u c u u c c a c a a a c c c a u At the time this research was initiated, certain observations were available to aid in the design of a hybrid ribosome binding site. Sherer et al. [Nucleic Acids Res. 8: 3895-3907 (1980)] had proposed a model ribosome binding site based on a computer analysis of 68 known *E. coli* ribosome binding sites. For R1 we chose to use this sequence after further modification. The first modification involved placing amino acid codons 3' to AUG that code for lymphoblastoid interferon amino acids. Wherever possible, model ribosome binding site nucleotide sequences were conserved. Additional sequence modifications were based on the analysis by Iserentant and Fiers on the translation efficiency of a series of recombinant plasmids containing various ribosome binding sites 5' to the cro gene [Gene, 9: 1-112 (1980)]. They concluded that an ideal ribosome binding site consists of a folded structure having a base paired stem-loop region with the AUG codon in the loop portion. Preferably the Shine and Dalgarno sequence would be 5' to the stem and in a single strand region. R1 was therefore modified to contain five base pairs formed from nucleotides on either side (86-90 and 96-100) of the AUG initiation codon. This was accomplished by further sequence changes in the model ribosome bindby screening known ribosome binding site sequences [Scherer, G. F. E. et al., (1980) Nucl. Acid. Res. 8: 3895-3907] from the AUG codon through the next seven codons (21 nucleotides) for DNA sequence homology with a cluster of potential lymphoblastoid interferon gene ribosome binding sites. This cluster was derived from all possible codons for the first eight amino acids of the lymphoblastoid interferon. Therefore, each nucleotide of a known ribosome binding site was compared with all possible nucleotides that could be inserted at the same relative position of the interferon gene while keeping its amino acid sequence constant. For example, R3 was derived from the φ X F protein ribosome binding site. The third codon in the φ X F ribosome binding site in AAU which codes for asparagine. For the lymphoblastoid gene, the third amino acid is aspartic acid having codons GAU and GAC. Therefore, if GAU is selected as the aspartic acid codon, a fit is possible for two of the three nucleotides at the same relative positions within the φ X F protein and R3 ribosome binding sites. Using this inspection procedure, all known ribosome binding sites were screened for possible homologies with the clustered set of potential lymphoblastoid gene sites. Several were identified where the maximum fit with the lymphoblastoid cluster over the first eight codons (24 nucleotides) was approximately 50%. Two of these (*E. coli* L11 protein and φ X F protein sites), which presumably are used to initiate translation of large amounts of protein, were selected as lymphoblastoid interferon ribosome binding sites. Wherever possible within the protein coding regions of these known sites (24 nucleotides), the DNA sequence was maintained. Certain nucleotides were, however, substituted so that lymphoblastoid amino acid sequences could be expressed rather tha either L11 or φ X F amino acids. The nucleotides 5' to the AUG codons in both the L11 and φ X F protein sites (26 nucleotides each) were maintained without modification as part of the R2 and R3 sites, respectively. Both design strategies appear to be valid as interferon hybrid protein is produced in 0.1-2 mg/OD$_{578}$ $_{nm}$ liter quantities from all three ribosome binding sites.

The lymphoblastoid gene sequence was obtained from the partial amino acid sequence of a human lymphoblastoid interferon produced by induction of Namalva cells with Newcastle disease virus, strain B1. The analysis covered 76% of the total protein and suggested that this lymphoblastoid interferon was not listed among the sequences of known human interferons derived via cDNA cloning or through DNA sequencing of genomic clones. [Goeddel, D. V. et al. (1981) Nature 290: 20-26; Stebbing, N. and Weck, P. K. (1983). In Recombinant DNA Products, Insulin, Interferons and Growth Hormones, A. Bollen, ed., CRC Press; Weissman, C. et al. (1982) UCLA Symp. Mol. Cell Biol. 25: 295-326.] Sequenced regions were amino acids 2-46, 60-85, and 112-166. These polypeptides were most analogous to the DNA sequences of IFN-αC, IFN-αI, and IFN-αF. In the region 2-46, there was only one amino acid difference between the lymphoblastoid peptides and the amino acid sequence of IFN-αF (leu 26 in the lymphoblastoid sequence was proline in IFN-αF). However, near the carboxyl terminus (112-166), the lymphoblastoid protein was more analogous to IFN-αC and IFN-αI. If this human lymphoblastoid interferon is analogous to all other α-interferons relative to size and general sequence, then a hybrid lymphoblastoid interferon can be derived. First the peptide sequences of the human lymphoblastoid interferon were alligned with the analogous positions in IFN-αC and incorporated into the lymphoblastoid hybrid gene at these same relative positions. Then IFN-αC peptide sequences were first used in place of the unknown lymphoblastoid interferon sequences (amino acids 47-59 and 86 to 111). Corresponding sequences of IFN-αF or IFN-αI can conveniently be substituted in place of the IFN-αC insertions at the 47-59 and 86-111 positions. However, it is known that IFN-αC is equivalent to IFN-αF at the 47-59 position. Thus the final interferon hybrid gene is a composite of these two presumably related proteins.

The present disclosure relates the detailed procedure involved in the synthesis of a hybrid interferon gene having αC leukocyte interferon inserts at the 47-59 and 86-111 positions. However, the corresponding leukocyte IFN-αF and IFN-αI sequences at these positions can be introduced by identical procedures. For example, new synthetic DNA fragments having sequences corresponding to leukocyte IFN-αF and αI at positions 47-59 and 86-111 can be synthesized. These segments can then be ligated to the appropriate lymphoblastoid sections to form the additional hybrid interferons. In the construction of these new genes, new restriction sites corresponding to the new sections would have to be used. These new sites can be identified by simply screening the entire gene for all possible restriction sites and using those that can be used most conveniently.

The DNA sequence of the lymphoblastoid hybrid interferon structural gene was based on several considerations. Initially, deoxyoligonucleotides were to be chemically synthesized and enzymatically joined to form the total gene. This total DNA duplex containing terminal EcoRI sites would then be cloned into the single EcoRI site of pUC8. These oligodeoxynucleotides were generally designed so as to maximize overlap between complementary segments and minimize overlap between the single stranded regions. Since the gene was designed for expression in *E. coli*, codons preferred by this organism were selected wherever possible. Additionally, certain codons were chosen so as to minimize or eliminate inverted and direct repeat sequences which could create serious problems during enzymatic ligation reactions. Chemically synthesized oligodeoxynucleotides were joined enzymatically to form four DNA duplexes containing 108 to 214 base pairs each. These four duplexes were then amplified individually in plasmids, isolated, sequenced and then sequentially joined through convenient restriction sites, and cloned to form the final gene. This plan is quite general and can be used even for much larger genes, since only relatively short duplexes (250 base pairs or so) are synthesized via chemical and enzymatic procedures.

Certain restriction sites were included which led to the successful cloning of the total gene as four sections. A restriction map of the lymphoblastoid hybrid interferon gene of the invention is presented in Table 3. It is likely that additional restriction enzymes will become known. The top portion of Table 3 is a schematic representation of the gene. Each 100 base pairs and the approximate location of restriction sites are marked. The precise position and sequence for various restriction sites are also listed.

TABLE 3

Restriction Map of the Lymphoblastoid Hybrid Interferon Gene

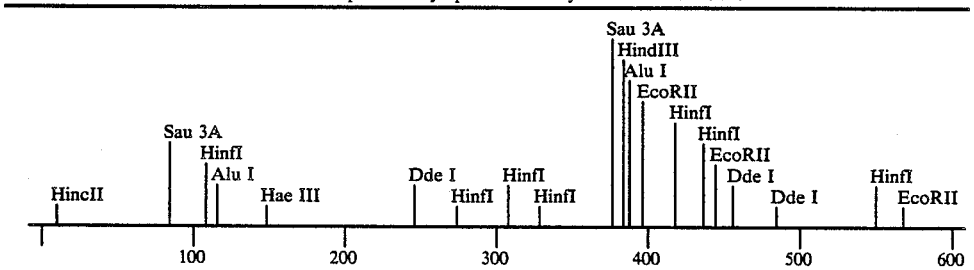

TABLE 3-continued
Restriction Map of the Lymphoblastoid Hybrid Interferon Gene

| Enzyme | Sequence | Site |
| --- | --- | --- |
| HincII | GTTGAC | 15 |
| Sau 3A | 'Gatc | 85, 377 |
| HinfI | G'A(T,C,A,G)TC | 109, 274, 308, 329, 418, 437, 550 |
| Alu I | AG'CT | 116, 385 |
| Hae III | GG'CC | 149 |
| Dde I | C'TY(A,C)AG | 246, 456, 485 |
| HindIII | AAGCTT | 384 |
| EcoRII | CC(A,T)GG | 397, 445, 568 |
| Mbo II | GAAGA(N$_8$) | 129, 215, 413, 493 |

Those restriction sites which were advantageously introduced are: HaeIII (position 149); DdeI (position 246); and HindIII (position 384). Using these three sites, the gene was cloned as Sections I (1-149), II (150-246), III (247-384), and IV (385-598). After amplification in E. coli as part of plasmids pBR322 or pUC8, each section was isolated and sequenced. Sections I and II were then joined enzymatically, cloned, and amplified as an EcoRI and DdeI restriction fragment. This combined duplex was next joined enzymatically to Section III, cloned as a EcoRI and HindIII fragment, amplified in E. coli and isolated after restriction with EcoRI and HindIII. Finally, this EcoRI and HindIII duplex was joined enzymatically to Section IV. The final gene was sequenced and tested for expression of α-interferon.

The structural gene, hybrid promoter, and three ribosome binding sites required the synthesis of 92 oligodeoxynuclotides (9 to 26 mononucleotides each). The synthetic plans for the structural gene, hybrid promoter, and ribosome binding site RI are shown in Table 1 above. Two major DNA synthesis methodologies were used. Oligodeoxynucleotides for the hybrid promoter and all three ribosome binding sites were synthesized using 5'-dimethoxytrityldeoxynucleoside-3'-methoxytetrazoylphosphoramidites as synthons and silica gel containing a covalently attached deoxynucleoside as the polymer support. After removal of protecting groups, the oligodeoxynucleotides were purified of various intermediates by polyacrylamide gel electrophoresis. The products can then be eluted from the gel. After passage through a short G50/40 Sephadex column to remove salts, buffers and solubilized gel material, the oligodeoxynucleotides were phosphorylated with [γ-$^{32}$P]ATP and T4-polynucleotide kinase. Results from analytical gel electrophoresis indicated that the products were homogeneous and ready to be used with T4 DNA ligase for preparing larger DNA duplexes.

In summary, the lymphoblastoid hybrid interferon gene of the invention was synthesized and cloned in four sections. These four sections were then joined to form the total gene. Thus, oligodeoxynucleotides containing from 10 to 25 mononucleotides each were synthesized chemically. Complementary segments contained protruding single strand regions for guiding the next segment into place. These segments were then joined enzymatically to form DNA duplexes containing up to 214 base pairs each. Using appropriate restriction sites, these gene sections can be amplified through cloning, isolated, and sequentially joined to one another to form the completely assembled gene. This plan is quite general and can be used to assemble genes of any size. Each section should be designed similar to Sections II and III. These two sections whose structural gene ends have high frequency restriction cutting sites were synthesized with linkers having restriction sites unique to the plasmid vector (EcoRI and HindIII). If necessary the gene segment can then be excised and separated from the plasmid using gel electrophoresis. The vector would migrate as one large fragment and the gene section as a small duplex containing 108-214 base pairs. Alternatively, the section can be excised directly from the plasmid using the high frequency cutting sites (in this case HaeIII and DdeI). This possibility can be used if the gene section duplex migrates in a unique region of the gel devoid of plasmid duplexes. Although not necessary, the synthesis would be somewhat simplified if the unique restriction sites were part of the structural gene rather than linker sequences. Section III is an example of this approach. Due to the redundancy of the genetic code and the large number of restriction enzymes that recognize different size base pair sequences, this alternative is usually possible.

The biological activity of various control regions and the lymphoblastoid hybrid interferon are of considerable interest. The promoter is a composite of three different promoter elements and the ribosome binding sites were designed for the interferon gene and do not correspond to any natural sequences. The interferon protein is a hybrid molecule composed of sequences from lymphoblastoid and leukocyte interferons. Sections of the novel hybrid interferon from C-type interferons represent a preferred embodiment of the invention. Optionally, αF- or αI-type leukocyte interferon sections may be substituted in place of αC-type interferon. All these structures (i.e., the hybrid control elements and the hybrid interferon) were quite active biologically.

The hybrid promoter was designed to be transcriptionally active but easily controlled. It contains elements of the λP$_R$ and T7 A2 promoters and the lac operator. Experimental results also show that transcription can be controlled with lac repressor and IPTG (Isopropyl β-D-thigalactoside).

The lymphoblastoid hybrid interferon was derived from two proteins. Approximately 76% was based on the amino acid sequence of a lymphoblastoid interferon produced by induction of Namalva cells with Newcastle disease virus, strain B1. The remainder was from the C subtype of the leukocyte interferons. This hybrid protein was as active biologically as known natural interferons. Already many α-interferons have been identified through cDNA cloning and sequencing. Additionally two natural hybrids formed from the A and D subtypes [Week, P. K., et al. (1981) Nucleic Acids Res. 9: 6153-6166] and a consensus interferon have been synthesized and shown to be biologically active. [Alton, K. et al. "Production, Characterization and Biological Efforts of Recombinant DNA Derived from Human IFN-α and IFN-γ Analogs. In The Biology of the Interferon System (1983) E. DeMaeyer and H. Schellekens, eds. Elsevier Science Publishers B.V.]. All these results suggest that the α-interferons are a rather diverse family of proteins. Additional modifications may therefore be possible in order to maximize biological activity, maximize yield, or perhaps simplify purification procedures. These modifications can best be accomplished if the gene is completely synthetic, cloned in sections, and readily accessible via various restriction enzymes. This same procedure will become generally useful for many different proteins. Questions of structure-function relationships can most rapidly be approached if a protein can be readily modified through amino acid changes. This flexibility in turn requires synthesis of at least major sections of a protein gene (perhaps between convenient, natural restriction sites).

The following examples further serve to illustrate the invention and are not intended to be limitative thereof.

EXAMPLE 1
Transcription Activity of the Hybrid Promoter

The hybrid promoter of the invention is a composite of the lambda $P_R$, the T7 A2 promoter, and the lac promoter (i.e., positions 5-45, 46-50, and 51-71 respectively; c.f., Table 1.

The transcription activity of this hybrid promoter was compared to the activity of the lac promoter. Both promoters were cloned into the same plasmid background and assayed for β-galactosidase activity in a lac deletion strain (71-18). Using this strain, the transcription activity of these two promoters was compared and the results are presented in Table 4.

Within the limits of this assay where similar promoter constructions are being tested in the same plasmid vector, the lambda $P_R$/T7 A2/lac hybrid promoter is approximately 50% more active than the fully induced lac

TABLE 4

| | Transcription Activity of the Hybrid Promoter[1] | |
|---|---|---|
| | Activity in β-Galactosidase Units[2] | |
| Promoter | Glucose | Glycerol |
| lac (wild-type) | 4800 | 10000 |
| $P_R$/T7 A2/lac | 18800 | 15500 |

[1] The synthetic lac promoter extended from position −74 to +21 of the natural lac promoter. This segment therefore included the lac promoter, lac operator, and the cyclic AMP receptor protein binding site as a completely base paired duplex. The $P_R$/T7 A2 promoter was the base paired duplex extending from 1 to 71 of the gene sequence shown in Table 1. These synthetic promoters were cloned into pRZ5605. The plasmid contains the lac Z gene, including the ribosome binding site sequence but lacks a promoter. Upstream from the lac Z gene are three restriction sites (EcoRI, SmaI; and BamHI). These blunt-end duplexes were introduced through the SmaI site and characterized by restriction mapping and DNA sequencing.
[2] β-galactosidase activity was measured on E. coli laboratory strain 71-18 using either glucose or glycerin as a carbon source.

promoter and approximately fourfold more active than the lac promoter under catabolite repression (glucose as the carbon source).

EXAMPLE 2
Preparation of Section I of the Hybrid Lymphoblastoid Gene

Section I corresponding to the sequence from 1-149 (c.f., Table 1) was prepared by two different approaches. The first approach involved isolation of the EcoRI-HaeIII fragment from an aberrant attempt to clone an EcoRI to HindIII duplex (nucleotides 1-384). The second approach was more direct. A duplex containing nucleotides 1-158 was synthesized in order to clone the EcoRI to HaeIII fragment (1-149).

The sequences and corresponding synthetic oligodeoxynucleotides for the first approach are shown in Table 5.

TABLE 5

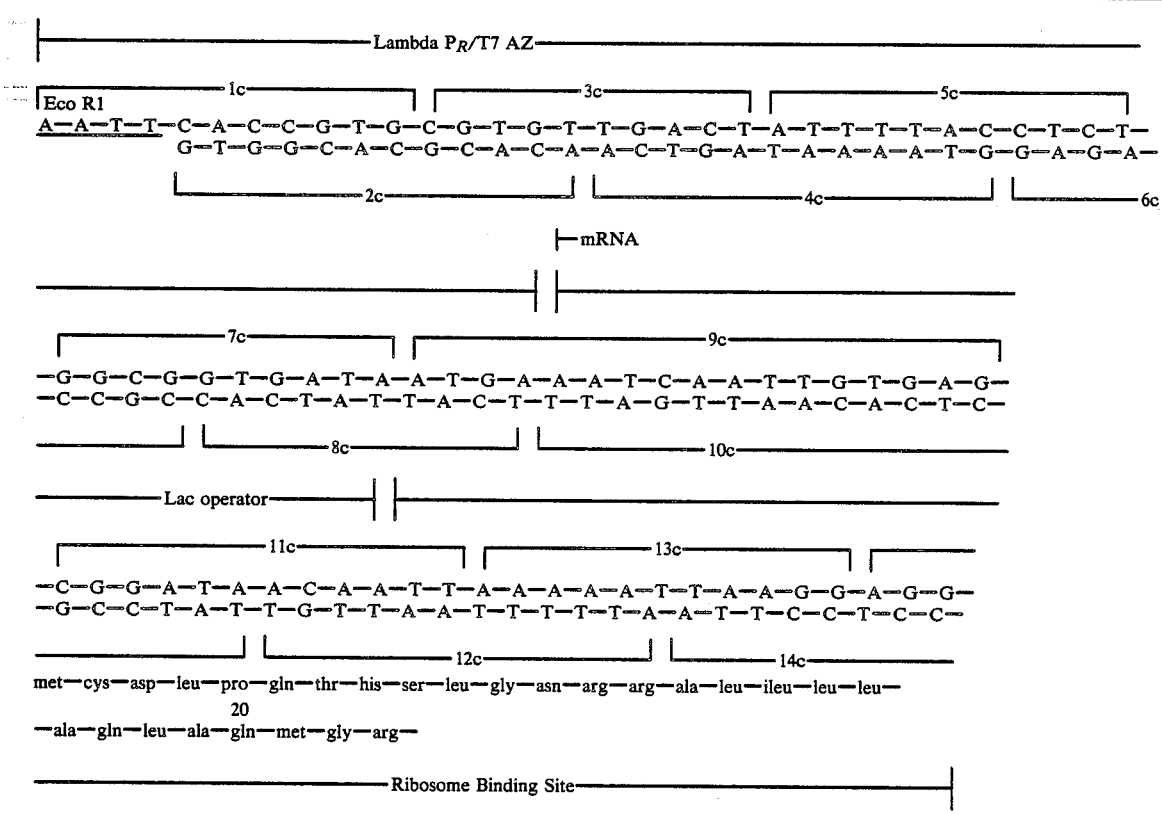

TABLE 5-continued
Enzymatic Ligation of Section I

```
         ┌──── 15c ────┐ ┌──── 17c ────┐ ┌──── 19c ────┐ ┌────
—A—T—C—A—C—T—A—T—G—T—G—T—G—A—T—T—T—G—C—C—G—C—A—G—A—C—T—C—A—T—A—G—
—T—A—G—T—G—A—T—A—C—A—C—A—C—T—A—A—A—C—G—G—C—G—T—C—T—G—A—G—T—A—T—C—
────┘ └──── 16c ────┘ └──── 18c ────┘ └──── 20c ────┘

┌──────── 1s ────────┐
—C—T—T—G—G—C—A—A—C—C—G—A—A—G—A—G—C—A—C—T—C—A—T—C—C—
—G—A—A—C—C—G—T—T—G—G—C—T—T—C—T—C—G—T—G—A—G—T—A—G—G—
└──────── 2s ────────┘

┌──── 3s ────┐ ┌──── 5s' ────┐
—T—G—T—T—G—G—C—C—C—A—A—T—T—G—G—C—C—C—A—A—A—T—G—G—T—C—G—C—A—
—A—C—A—A—C—C—G—G—G—T—T—A—A—C—C—G—G—G—T—T—T—A—C—C—A—G—C—G—T—
└──── 4s ────┘                  └──── 6s' ────┘
            30                                40
ileu—ser—leu—phe—ser—cys—leu—lys—asp—arg—his—asp—phe—gly—phe—pro—gln—glu—glu—phe—asp—gly—
                50
—asn—gln—phe—gln—lys—ala—gln—ala—ileu—ser—val—leu ┌──── 7s ────┐ ┌──── 9s ────┐
—T—T—T—C—C—C—T—G—T—T—C—T—C—G—T—G—C—C—T—T—A—A—A—G—A—C—C—G—C—C—A—C—G—
—A—A—A—G—G—G—A—C—A—A—G—A—G—C—A—C—G—G—A—A—T—T—T—C—T—G—G—C—G—G—T—G—C—
            └──── 8s ────┘           └──── 10s ────┘

┌──── 11s ────┐ ┌──── 13s ────┐
—A—T—T—T—C—G—G—G—T—T—T—C—C—A—C—A—G—G—A—A—G—A—G—T—T—T—G—A—C—G—G—C—
—T—A—A—A—G—C—C—C—A—A—A—G—G—T—G—T—C—C—T—T—C—T—C—A—A—A—C—T—G—C—C—G—
            └──── 12s ────┘          └──── 14s ────┘

┌──── 15s' ────┐ ┌──── 17s' ────┐
—A—A—T—C—A—G—T—T—C—C—A—A—A—A—G—G—C—T—C—A—G—G—C—A—A—T—C—T—T—C—
—T—T—A—G—T—C—A—A—G—G—T—T—T—T—C—C—G—A—G—T—C—C—G—T—T—A—G—A—G—
            └──── 16s' ────┘         └────
        60                            70
—his—glu—met—ileu—gln—gln—ileu—phe—asp—leu—phe—ser—thr—lys—asp—ser—ser—ala—ala—trp—asn—glu—
       80                          90
—ser—leu—leu—asp—lys—phe—ser—thr—glu—leu—tyr—

┌──── 19s' ────┐ ┌──── 21s' ────┐
—G—G—T—T—C—T—G—C—A—T—G—A—G—A—T—G—A—T—T—C—A—G—C—A—A—A—T—C—T—T—C—A—
—C—C—A—A—G—A—C—G—T—A—C—T—C—T—A—C—T—A—G—T—C—G—T—T—T—A—G—A—A—G—T—
└──── 18s' ────┘           └──── 20s' ────┘

┌──── 23s' ────┐
—A—C—C—T—G—T—T—C—T—C—C—A—C—T—A—A—A—G—A—C—T—C—T—T—C—G—G—C—T—G—C—T—
—T—G—G—A—C—A—A—G—A—G—G—T—G—A—T—T—T—C—T—G—A—G—A—A—G—C—C—G—A—C—G—A—
            └──── 22s' ────┘         └──── 24s' ────┘

┌──── 25s' ────┐ ┌──── 27s' ────┐
—T—G—G—A—A—C—G—A—A—T—C—C—T—T—G—C—T—T—G—A—T—A—A—A—T—T—C—T—C—C—
—A—C—C—T—T—G—C—T—T—A—G—G—A—A—C—G—A—A—C—T—A—T—T—T—A—A—G—A—G—G—
            └──── 26s' ────┘          └──── 28s' ────┘
                                   100
gln—gln—leu—asn—asp—leu—glu—ala—cys—val—ileu—gln—glu—val—gly—

┌──── 29s ────┐
—A—C—T—G—A—A—C—T—C—T—A—T—C—A—G—C—A—A—A—C—T—G—A—A—C—G—A—T—C—T—
—T—G—A—C—T—T—G—A—G—A—T—A—G—T—C—G—T—T—T—G—A—C—T—T—G—C—T—A—G—A—
            └──── 30s ────┘

┌── 31s ──┐ Hind III ┌──── 33s ────┐
—T—G—A—A—G—C—T—T—G—C—G—T—T—A—T—C—C—A—G—G—A—G—G—T—A—G—G—C—G
—A—C—T—T—C—G—A—A—C—G—C—A—A—T—A—G—G—T—C—C—T—C—C—A—T—C—C—G—C
            └──── 32s ────┘
```

The DNA sequence from the EcoRI site 5' to the promoter through segment 33s is shown. The HindIII site is also shown. Brackets with enclosed letters and numbers define the various DNA segments that were chemically synthesized. The letters c and s designate control region and structural gene regions, respectively. The hybrid promoter, lac operator, and R1 ribosome binding site approximately occupy sequences 1c–11c, 9c–12c, and 13c–20c, respectively. The ATG initiation condon sequence within R1 is found in 17c.

The synthetic fragments shown in Table 5 were first joined to form three duplexes comprising segments 1c to 20c, 1s to 28s', and 29s to 33s. These three duplexes were then joined to form a duplex containing 1c to 33s. The synthesis of duplex 1c–20c was completed via three T4-DNA ligase catalyzed ligation steps. Segments 3c to 10c and 11c to 20c were independently synthesized. Each duplex product was purified from unligated segments by gel permeation column chromatography on Sephadex G150/40 and analyzed by gel electrophoresis. The final step was a multiple ligation involving duplex 3c–10c (5 pmole), duplex 11c–20c (5 pmole), [5'-$^{32}$P] segment 2c (10 pmole) and unphosphorylated 1c (20 pmole). The gel analysis of this ligation reaction was performed. In addition to unreacted starting materials (duplexes 1c–10c and 11c–20c) and product (duplex 1c–20c), two uncharacterized intermediates were also identified by gel electrophoresis. [5'-$^{32}$P] Segment 2c migrates from the gel. Duplex 1c–20c containing segments composed of 113 and 115 mononucleotides was freed of duplexes 1c–10c and 11c–20c by chromatography on a Sephadex G150/40 column. Gel electrophoresis analysis of this purification step indicates that the two uncharacterized intermediates still remain in the sample of duplex 1c–20c. The yield of duplex 1c–20c was 1.5 pmole. The removal of duplex 11c–20c was especially critical. This duplex has the same single stranded region adjacent to the structural gene as does duplex 1c–20c. If duplex 11c–20c were not removed, it would compete with duplex 1c–20c for the structural gene duplex during the next appropriate ligation step.

Duplex 1s–28s' containing structural gene segments 1s to 28s' was sythesized in a stepwise manner. Segments 1s to 4s, 5s' to 10s, 11s to 14s', 15s to 18s', 19s' to 24s', and 25s' to 28s' were joined to form intermediate duplexes and column purified. The first step in the final assembly was synthesis of duplex 1s–10s by joining duplex 1s–4s to 5s–10s followed by gel permeation chromatography on Sephadex G150/40. Gel electrophresis analysis of the column chromatography purified duplex 1s–10s (90 pmole) clearly shows that most of the duplexes 5s–10s and 1s–4s have been removed. This sample of duplex 1s–10s was next joined to duplex 11s–14s' to form duplex 1s–14s' (45 pmole). After gel permeation column chromatography, excess duplex 11s–14s' had been removed as can be seen by gel electrophoresis analysis. Duplex 1s–14s' however was contaminated with unreacted duplex 1s–10s. This growing duplex was then reacted sequentially with duplexes 15s'–18s', 19s'–24s', and 25s'–28s' to form duplexes 1s–18s; (20 pmole), 1s'–24s' (45 pmole), and 1s'–28s'. Each intermediate duplex was purified by Sephadex G150 column chromatography and analyzed by gel electrophoresis. Clearly the gel permeation technique did remove each new, relatively small duplex but failed to remove unreacted, partially extended duplexes. These incomplete duplexes were carried forward and constitute most of the DNA present in the final sample of duplex 1s–28s'. The final step was purification of doplex 1s'–28s' by preparative gel electrophoresis. The appropriate band was cut from the gel, eluted, and purified from salts and buffers. The isolated yield of duplex 1s–28s' was 1 pmole.

Duplex 29s–33s was prepared. After enzymatic joining of these segments, the duplex was purified by column chromatography in Sephadex G 150/40 and analyzed by gel electrophoresis.

Duplex 1c–33s was prepared by joining duplexes 1c–20c, 1s'–29s', and 29s–33s. Duplex 1c–20c (1.25 pmole), duplex 1s–28s' (0.53 pmole) and duplex 29s–33s (5 pmole) were each annealed from 75° C. Duplex 1s–28s' and duplex 29s–33s were then mixed, warmed to 45° C. and cooled to room temperature. Duplex 1c–20c was next added. The solution was warmed to 37° C. and cooled initially to room temperature and then to 4° C. The final volume was 15 μl. After addition of T4-DNA ligase (2.5 units), the reaction was allowed to proceed overnight. The total reaction mixture was fractionated by gel electrophoresis. Size markers generated from pBR322 digestion by HpaII were used. The final yield of duplex 1c–33s, as purified from this gel, was 50 femtomole.

Analysis by gel electrophoresis of the reaction indicated that the ligation reaction only proceeded 10–20%. Major bands of unreacted duplexes 1c–20c, 1s–28s', and 29s–33s were present on the gel. The product was eluted from the appropriate gel slice and digested with HindIII in order to generate a duplex ready for cloning in pBR325.

Synthesis of Section I via the second approach focused on the EcoRI to HaeIII region of the structural gene. The sequence and synthesis plan are shown in Table 6.

TABLE 6

Synthetic Plan and Structural Gene Sequence for Section I from EcoRI to HaeIII

Section I EcoRI-HaeIII

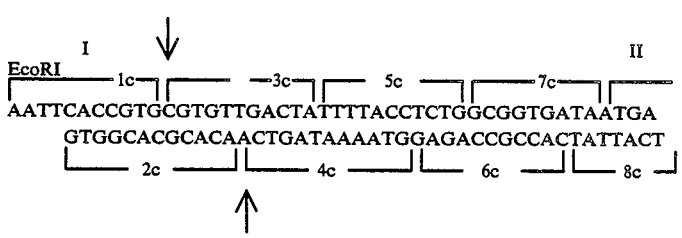

TABLE 6-continued
Synthetic Plan and Structural Gene Sequence for Section I from EcoRI to HaeIII

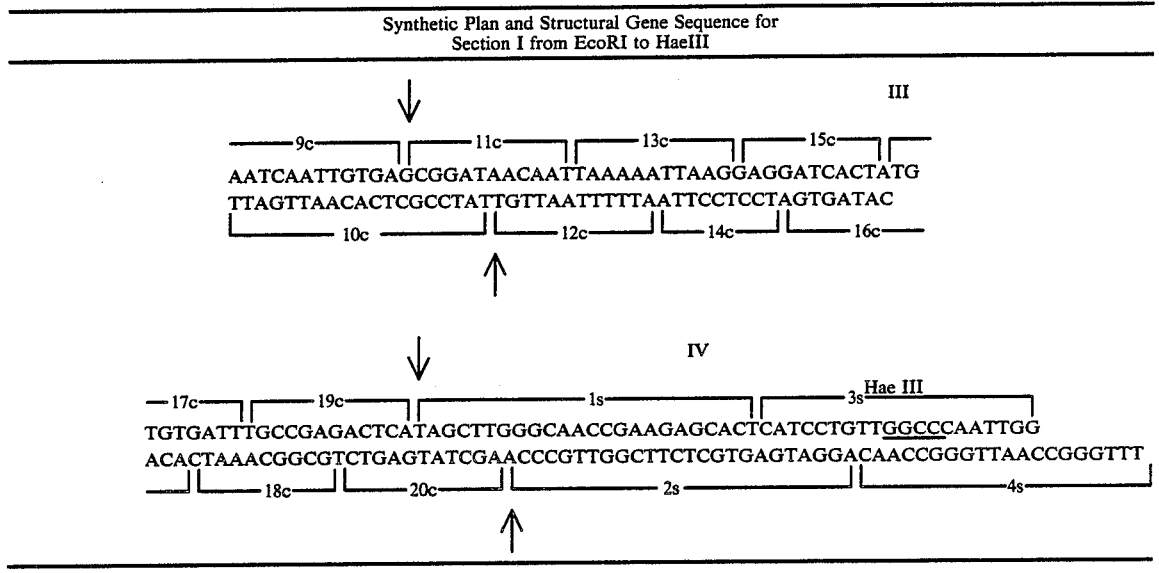

The lymphoblastoid interferon hybrid gene from the 5' EcoRI site on the sense strand through the HaeIII site at 149 is depicted. Brackets with numbers enclose chemically synthesized segments. Segments 1c through 20c are the same as described in Table 5. Therefore, the hybrid promoter, lac operator, and R1 ribosome binding site occupy approximately sequences 1c–11c, 9c–12c, and 13c–20c, respectively. The ATG initiation codon sequence within R1 is found in 17c. Duplex 1c–20c (1.5 pmole), whose synthesis has been described, and duplex 1s–4s (15 pmole) were annealed from 37° C. and mixed. After annealing from 37° C. to 4° C., T4-DNA ligase was added and the reaction allowed to proceed overnight. Analysis of the reaction mixture by gel electrophoresis was performed. Size markers generated from pBR322 by restriction with PhaII were used. The product, duplex 1c–4s, as eluted from the gel, was isolated in 0.6 pmole yield. Once synthesized, fragment I can be cloned into pBR322 opened with the restriction enzymes EcoRI and BalI. Section I was synthesized from duplex 1c–20c and duplex 1s–4s. Duplex 1s–4s was synthesized in the usual manner and purified using a Sephadex G 150 column. The next step was joining duplex 1s–4s in tenfold molar excess to duplex 1c–20c. An analytical gel of the reaction mixture suggested that conversion to the final product (duplex 1c–4s) was quite satisfactory. The isolated yield (40%) confirmed these results.

EXAMPLE 3
Preparation of Section II of the Hybrid Lymphoblastoid Gene

Section II containing EcoRI and HindIII sites and extending from the HaeIII site (position 149) to the DdeI site (position 246) of the interferon gene is shown in Table 7.

TABLE 7
Synthetic Design and Structural Gene Sequence for Section II from HaeIII to DdeI Section II Hae III-DdeI

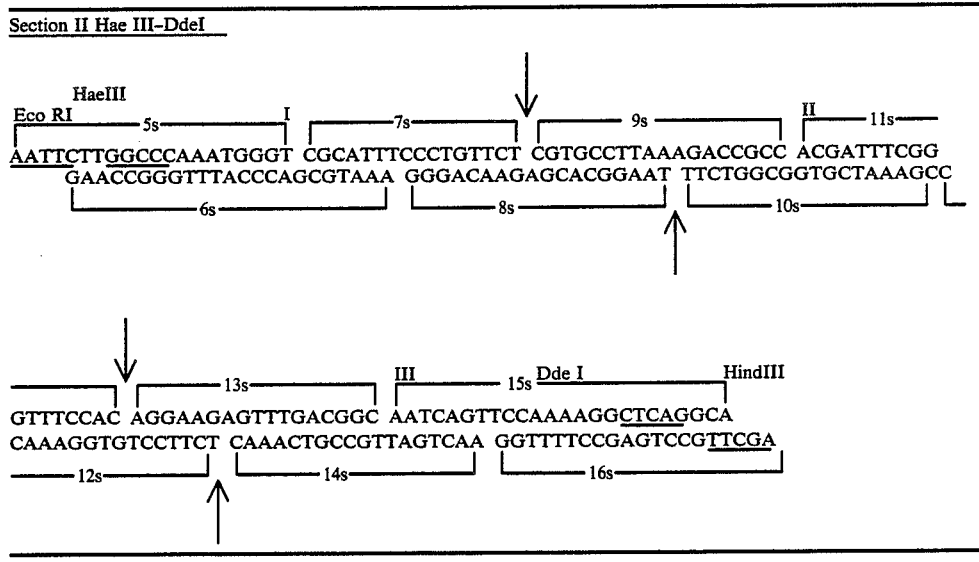

This arrangement of restriction sites was used to clone Section II between the unique EcoRI and HindIII sites of pUC8. Restriction enzyme cleavage of the cloned gene fragment in pUC8 with HaeIII and DdeI generated Section II as a unique duplex containing the interferon gene sequences. Duplex 5s–16s corresponding to Section II was prepared in two steps. In the first step, [5'-$^{32}$P]-Labeled segments 5s–8s, 9s–12s, and 13s to 16s were annealed and ligated in three separate test tubes as previously described (400 pmole of each segment). These three ligated duplexes were then purified on Sephadex G 150/40 column, pooled, annealed together from 37° C. and joined using T4-ligase (5 units). The results of this ligation were evaluated by gel electrophoresis. The final product, duplex 5s–16s containing 113 mononucleotides in each strand, was isolated and purified by preparative gel electrophoresis and characterized as to size against calibrated DNA markers. The isolated yield was 60 pmole. An aliquot of the purified duplex was analyzed by gel electrophoresis using pBR322 DNA cut with HpaII as size markers. The product migrated as expected relative to these size markers. As determined by gel analysis, the major ligation product was an intermediate duplex which has not been characterized. Such intermediates can be generated by several mechanisms. The most trivial explanation is a stoichiometry problem. If unequal molar ratios of all [5'-$^{32}$P]-labeled oligodeoxynucleotides are used in a ligation reaction, then an intermediate corresponding in yield to the limiting reagent will be the major product. More often, however, the formation of either intramolecular or intermolecular secondary complexes lead to the accumulation of intermediates. These complexes are not easily predicted. Such problems are most readily solved by resynthesis using different positions for generating overlapping and complementary single strand oligodeoxynucleotides.

EXAMPLE 4

Preparation of Section III of the Hybrid Lymphoblastoid Gene

The DNA sequence of the structural gene of Section III, the duplex 17s–28s containing an EcoRI site and extending from the DdeI site at position 246 to the HindIII site at position 384 of the interferon sequence, is shown in Table 8.

Synthetic Design and Structural Gene Sequences
for Section III from DdeI to HindIII
Section III DdeI–HindIII

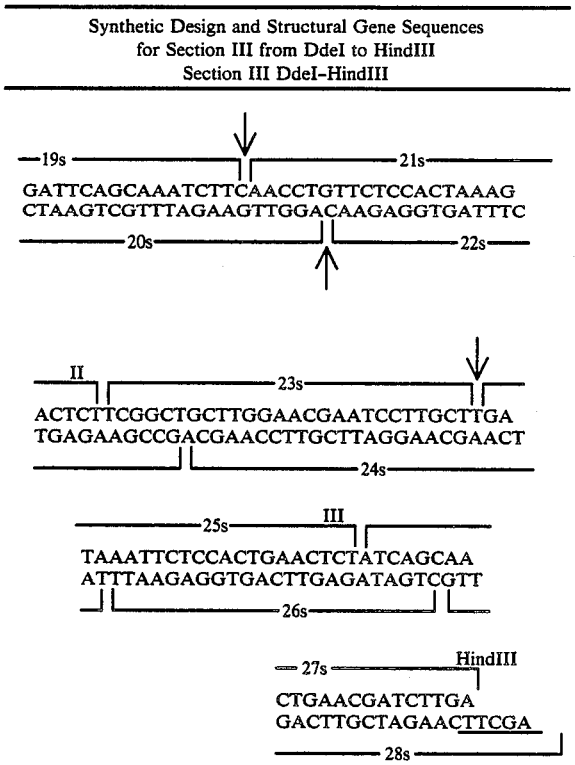

The arrangement of restriction sites described in Table 8 was used to clone Section III between the unique EcoRI and HindIII sites of pUC8. Restriction enzyme cleavage of the cloned gene fragment in pUC8 with DdeI and HindIII generated Section III as a unique duplex. [5'-$^{32}$P]-Labeled segments 17s to 20s (100 pmole each), 21s to 24s (100 pmole each), and 25s to 28s (100 pmole each) were annealed and ligated in three separate test tubes. These duplexes were then mixed without purification and enzymetically joined using T4 ligase. The reaction mixture was evaluated by gel electrophoresis. A major band corresponding to intermediates (duplex 17s–24s or 21s–28s) was observed. The generation of many intermediates was presumably due to the presence of unligated segments during the joining steps. The final product, as two oligodeoxynucleotides containing 146 mononucleotides each, was isolated in a purified form (13 pmole; 26% yield) by preparative gel electrophoresis. An aliquot of the purified duplex was characterized as to size by gel electrophoresis using pBR322 DNA cut with HpaII as size markers. The yield of purified duplex 17s–28s (Section III) was 13 pmole (26% yield).

EXAMPLE 5

Preparation of Section IV of the Hybrid Lymphoblastoid Gene

Section IV of the hybrid lymphoblastoid gene of the invention extends from the HindIII (position 385, c.f., Table 1) site to the EcoRI site at the end of the gene. The DNA sequence of the structural gene is shown in Table 9 from position 351 to the end of the gene at the EcoRI site.

TABLE 9

Synthetic Design and Structural Gene Sequence for Section IV from HindIII to EcoRI
Section IV HindIII–EcoRI

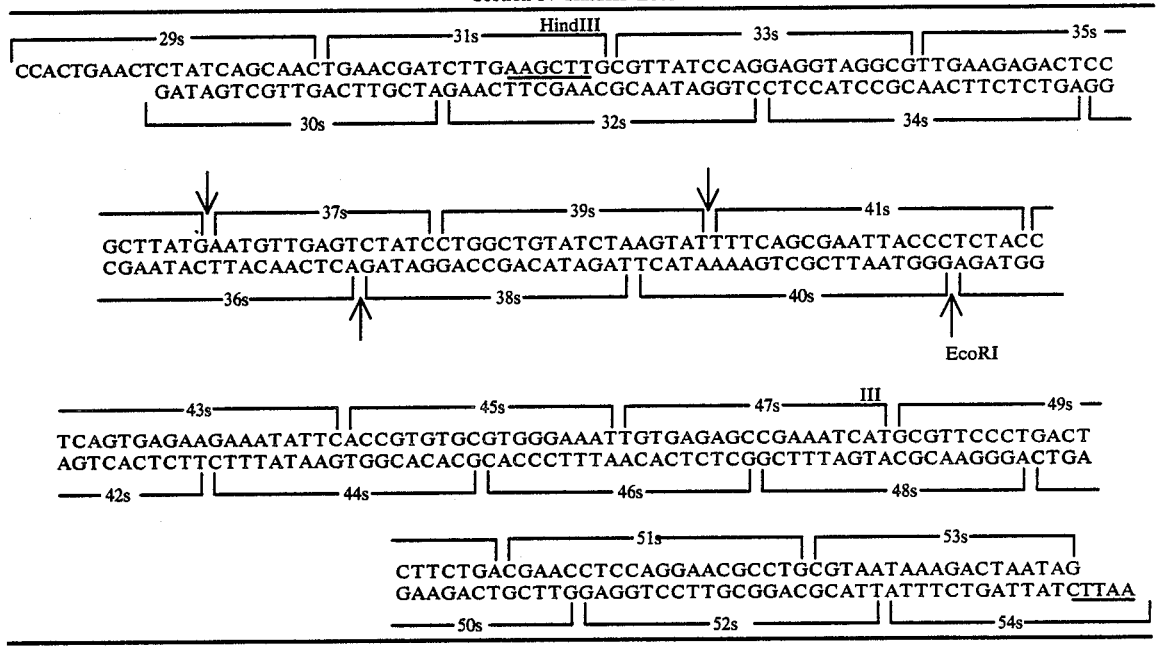

As a first step, [5'-32P]-labeled segments 29s to 36s, 37s to 40s, and 41s to 54s were enzymatically joined independently to form the appropriate intermediate DNA duplexes. Each of these three duplexes was then purified and joined in stepwise fashion. Each duplex was purified from unreacted segments by column chromatography on Sephadex G 150/40 and analyzed by gel electrophoresis after purification. The gel obtained after purification of 41s–54s showed that the DNA strands containing 135 and 123 mononucleotides have separated. Duplexes 37s–40s (45 pmole) and 41s–54s (10 pmole) were enzymatically joined using T4-DNA ligase. The product (duplex 37s–54s) of this ligation was fractionated from starting materials on a Sephadex G 150/40 column. The isolated yield was 2.5 pmole (25%). The purified duplex was analyzed by gel electrophoresis. Duplex 37s–54s (2.5 pmole) and duplex 29s–36s (10 pmole) were enzymatically joined and the reaction mixture fractionated by column chromatography on Sephadex G 150/40. The final product (duplex 29s–54s, 1.6 pmole) was analyzed by gel electrophoresis. A series of size markers generated by a HpaII cut of pBR322 was used in this gel analysis. Based on the limiting reagent (duplex 41s–54s), the overall yield of partially purified duplex 29s–54s was 16%. The column purification step successfully removed unreacted duplex 29s–36s but failed to remove duplex 37s–54s from the product.

EXAMPLE 6

Cloning the Lymphoblastoid Hybrid Interferon Gene

Figure 2:
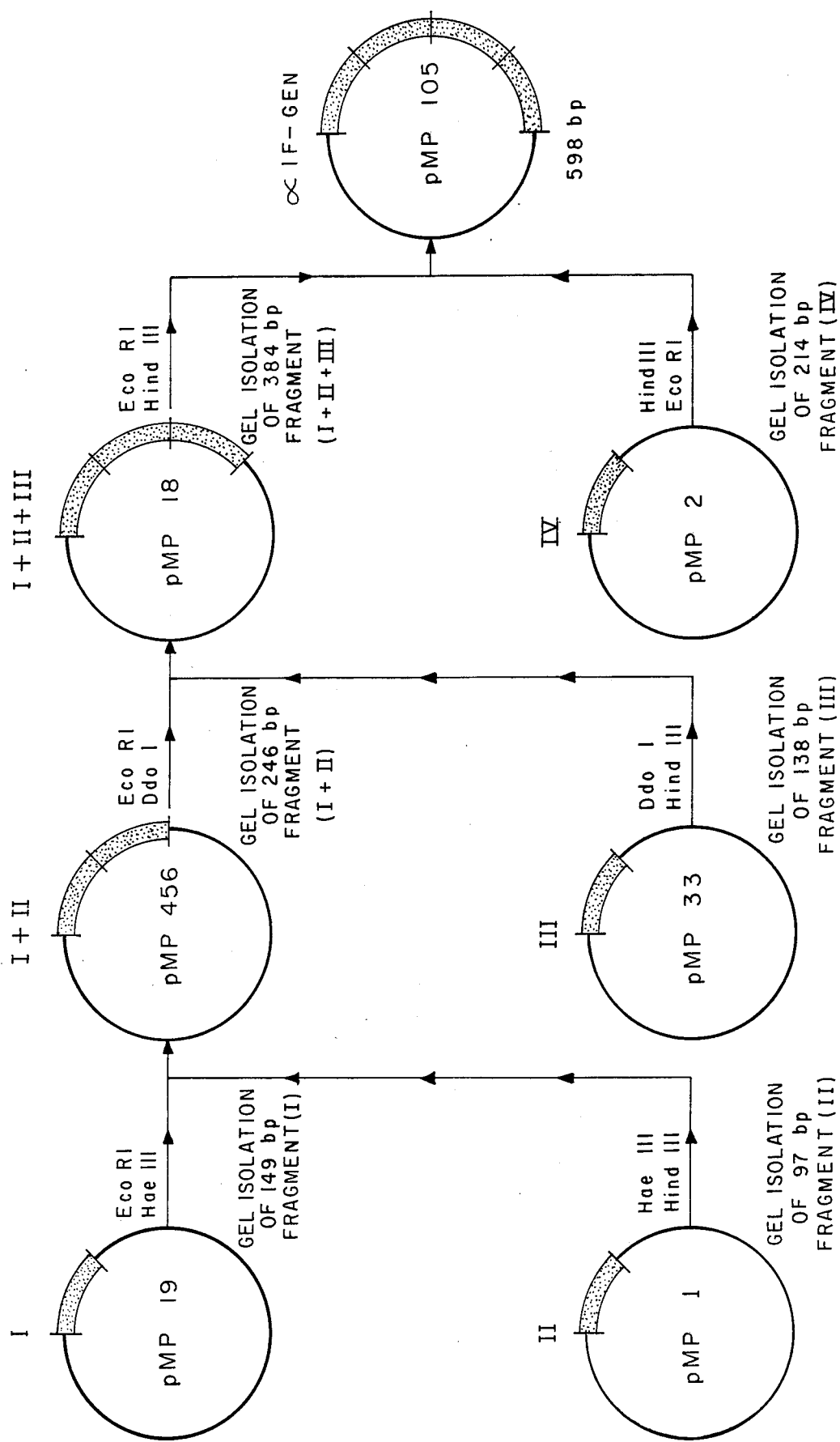
FIG. 2: A schematic outline showing plasmid derivatives containing interferon gene sections, including construction sequences for the interferon gene.

Successful cloning of the four subfragments of the 598 b.p. lymphoblastoid hybrid interferon gene and assembly of the total gene was accomplished using the procedure outlined in FIG. 1. The top portion of FIG. 1 shows schematically the interferon gene with the key restriction sites. The central portion shows the four sections as cloned in plasmids and the bottom portion schematically outlines the plan for stepwise joining these sections. Thus, the gene was initially cloned in four sections. These sections were then joined sequentially and cloned in three steps to form the total gene. The results summarizing these steps are presented in FIG. 2. Plasmid derivatives schematically outlining key gene sections are shown. Section I, which extends from the 5' EcoRI site to the HaeIII cut site at position 149, was isolated from an unsuccessful attempt to clone from EcoRI to the HindIII cut site at position 384. When the synthetic duplex extending from the 5' EcoRI site (relative to the sense strand) to the HindIII site was cloned into pBR325, only a clone containing part of the interferon sequence could be isolated. This clone had a deletion from position 223 to 372 (or 225 to 374). However, the sequence from the 5' EcoRI site to the HaeIII cut site was intact. This gene segment as a pBR325 derivative (pMP19) was used to isolate Section I. Section II containing structural gene sequences from the HaeIII site to the DdeI site at position 246 was cloned (pMP1) with EcoRI and HindIII linkers. In this way, cloning, isolation and sequencing as a unique EcoRI-HindIII duplex could be easily accomplished in pUC8. Similarly, Section III containing structural gene sequences from the DdeI site at position 247 to HindIII was cloned (pMP33) with an EcoRI linker, Section IV which extends from the HindIII cut site at 384 to the EcoRI site at the 3'-end of the structural gene was inserted into pUC8 which had been opened with EcoRI and HindIII. The resulting plasmid (pMP2) was characterized to contain Section IV by DNA sequencing.

After amplification of the cloned gene fragments in vivo, the segments were isolated and assembled stepwise in pUC8. Section I was isolated from pMP19 by treatment with EcoRI and HaeIII restriction enzymes followed by fractionation using 10% polyacrylamide gel electrophoresis. Similarly, Section II was isolated from pMP1 after treatment with HaeIII and HindIII. The two segments were recovered from the gel, joined using T4-DNA ligase, and cloned into pUC8 that had been opened with EcoRI and HindIII enzymes. Clones containing the appropriate 246 base pair duplex extending from the 5' EcoRI site to the DdeI site (Section I-II) were identified (pMP456). Section I-II was recovered from pMP456 by first treatment of the plasmid with EcoRI and DdeI enzymes and then preparative gel electrophoresis. Similarly, Section III was recovered from pMP33 by enzymatic digestion with DdeI and HindIII. Section I-II was next joined to Section III through the common DdeI site and the product (Section I-II-III) was cloned into pUC8. A plasmid containing Section I-II-III was isolated (pMP18) and characterized by restriction analysis. The final step involved the ligation of the Section I-II-III with Section IV. Section I-II-III and Section IV were isolated from pMP18 and pMP2, respectively, by enzymatic treatment with EcoRI and HindIII followed by isolation using preparative polyacrylamide gel electrophoresis. After joining these two sections with T4-DNA ligase and cloning into pUC8, the correct assembly of the gene in pMP105 was verified by restriction enzyme analysis and DNA sequence determination. Clones containing the interferon gene in both orientations with respect to pUC8 were obtained.

EXAMPLE 7

Incorporation of Ribosome Binding Sites R2 and R3 into the Hybrid Lymphoblastoid Gene The interferon gene as initially assembled (c.f., FIGS. 1 & 2) contained ribosome binding site R1. In order to maximize the possibility for high level expression of this gene, two additional ribosome binding sites, R2 and R3, were constructed. In this way, translation initiation from three different ribosome binding sites could be rigorously checked since no changes in nucleotide sequence were introduced in either the promoter or structural gene. The chemically synthesized segments corresponding to R2 and R3 were assembled as EcoRI-AluI duplexes. Therefore each duplex contained the first nine codons of the interferon gene and the entire control region including the $\lambda P_R/T7$ A2 promoter, lac operator, and the appropriate ribosome binding site.

Preparation of the EcoRI-AluI duplex containing ribosome binding site R2. The DNA sequence of the R2 duplex is shown in Table 10.

TABLE 10

Preparation of the EcoRI-AluI Duplex Containing Ribosome Binding Site R2

Table 10 shows the duplex extending from EcoRI through AluI and including segments 1s and 2s of the structural gene. As can be seen by comparison with the R1 control region (c.f., Table 5), segments 1c to 11c and 1s, 2s corresponding to the promoter-lac operator and the first two structural gene segments, respectively, are identical. The ribosome binding site sequences for R1 (12c-20c) and R2 (21c-29c) are different. Unphosphorylated 1c (200 pmole) and [5'-$^{32}$P]-labeled 2c were annealed from 75° C. in 8 μl ligase buffer. Preformed duplex 3c-10c carrying [5'-$^{32}$P]-labels (80 pmole) was dissolved in 8 μl ligase buffer, pooled with 1c and 2c, and the mixture annealed from 37° C. These segments were then combined with preformed duplex 21c-29c carrying [5'-$^{32}$P]-labels (60 pmole) and the mixture annealed from 35° C. The final volume was 40 μl. T4-DNA ligase (5 units) was added and the joining reactions allowed to proceed overnight. [5'-$^{32}$P]-labeled segments 1s and 2s (100 pmole each) and T4-DNA ligase (2.5 units) were added and incubation was continued for six additional hours at 4° C. The ligation mixture was dried in vacuo, redissolved in 40 μl formamide, heated in a boiling water bath for 3 minutes, and loaded on to an 8% acrylamide gel containing 8M urea. The band of acrylamide containing the R2 product duplex (1c-2s) was cut from the gel and the duplex extracted and precipitated with ethanol. The final yield was 6.5 pmole. Duplex 1c-2s (5 pmole) was annealed from 75° C. in 10 μl restriction buffer and then treated with AluI (10 units) at 37° C. for 2 hours. The products obtained from this restriction cleavage were analyzed by gel electrophoresis. The small duplex generated from 1s and 2s by cleavage at the AluI site was found near the bottom of the gel. The slowest migrating band corresponded to the unrestricted duplex. The EcoRI-AluI duplex migrated as separated strands and was the major $^{32}$P-labeled band. Size markers generated from HpaII cleavage of pBR322 were used. The AluI digested duplex was fractionated on a Sephadex G 150/40 column and analyzed by gel electrophoresis. The column eluant contained the EcoRI-AluI duplex of R2 and undigested duplex 1c-2s. The recovery was 3.5 pmole.

Preparation of the EcoRI-AluI duplex containing ribosome binding site R3. The DNA sequence of the R3 duplex is shown in Table 11.

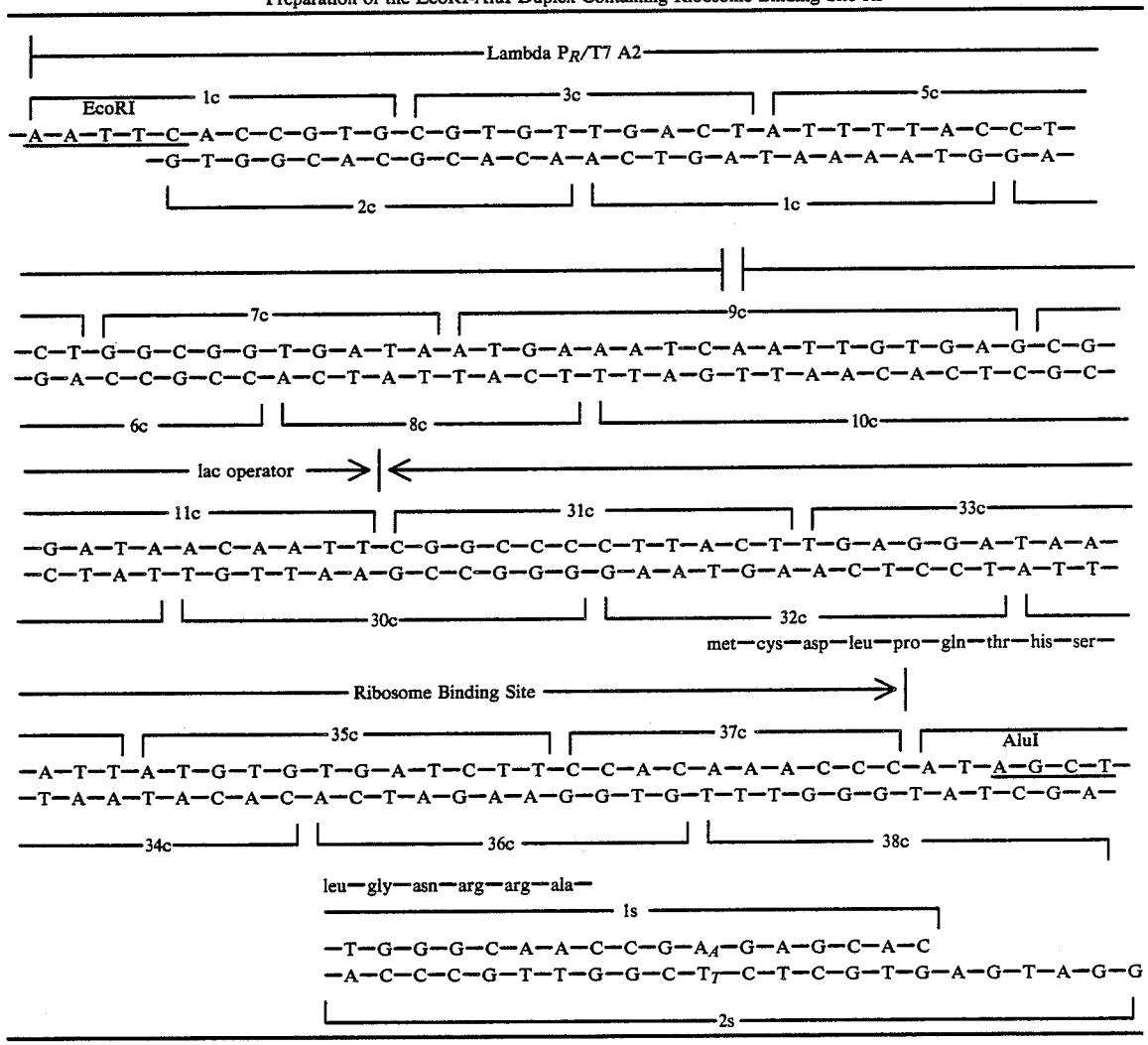

Table 11 shows the duplex extending from EcoRI through AluI and including segments 1s and 2s of the structural gene. As can be seen by comparison with the R1 control region (c.f., Table 5), segments 1c to 11c and 1s, 2s corresponding to the promoter-lac operator and the first two structural gene segments, respectively, are identical. The ribosome binding site sequences for R1 (12c-20c) and R3 (30c-38c) are different. The ligation of these segments to form a duplex 1c-2s containing R3 was completed in the same manner as described above for the synthesis of the same duplex containing R2 sequences. Amounts of segments were as follows: 1c (320 pmole); 2c (160 pmole); 3c-10c (80 pmole); 29c-38c (60 pmole); 1s (100 pmole); 2s (100 pmole). The final yield was 14 pmole. After digestion with AluI as described above, the EcoRI-AluI duplex containing R3 was isolated in 3.5 pmole yield from 5 pmole of duplex 1c-2s. The results of this synthesis were analyzed by gel electrophoresis.

The duplex 1c-2s was purified by column chromatography as previously described. Using size markers generated by digestion of pBR322 with HaeII, the following were analyzed by gel electrophoresis: ligated and column-purified duplex 1c-2s; the reaction mixture from duplex 1c-2s after digestion with AluI; and column-purified AluI digestion mixture. pBR322 was opened with the restriction enzymes EcoRI and PuuII. R1 and R2 were cloned separately into the opened plasmid as EcoRI-AluI fragments.

Figure 3:
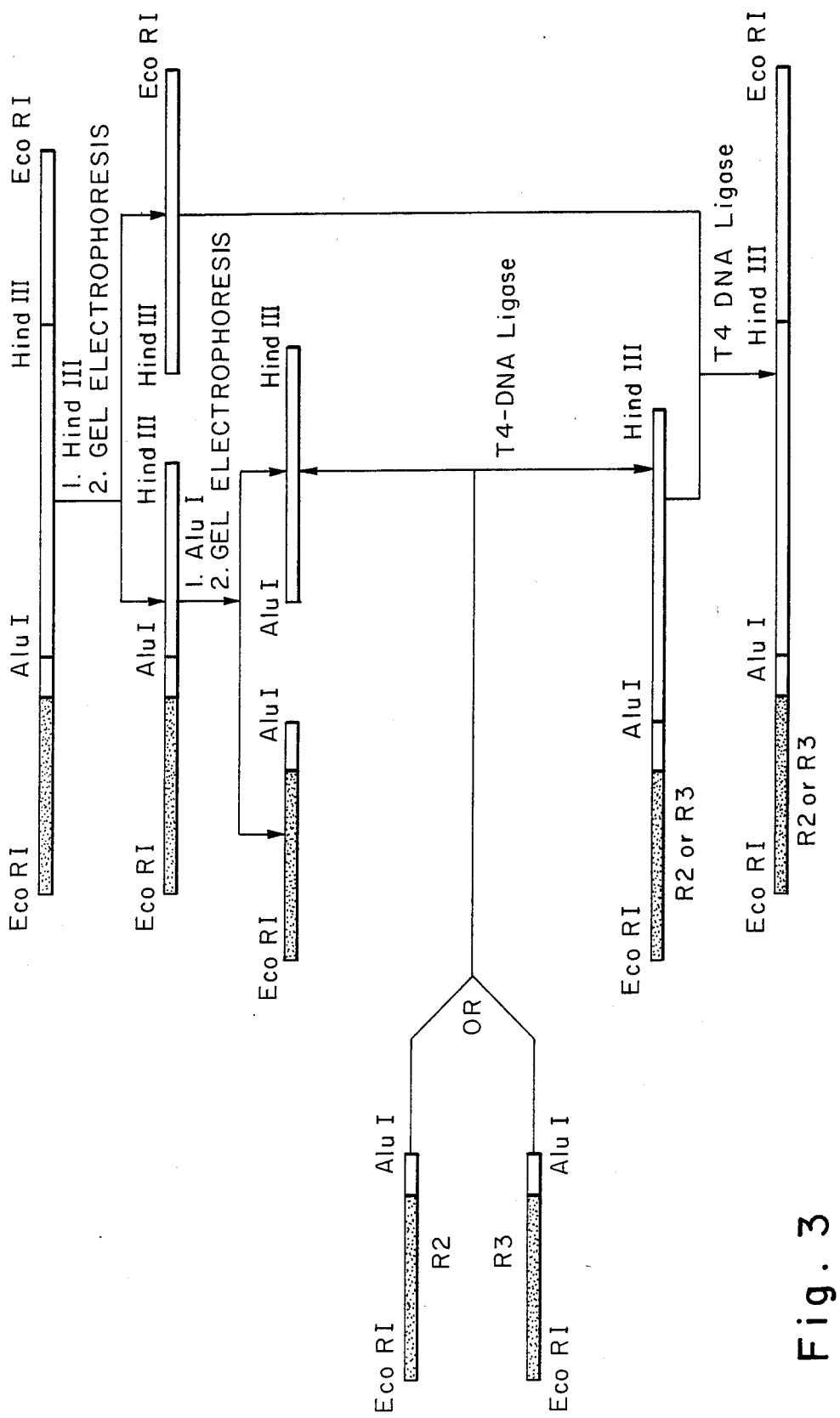
FIG. 3: A schematic outline describing the assembly of the interferon gene containing ribosome binding sites R2 and R3 is presented.

Assembly of the hybrid interferon gene containing ribosome binding sites R2 and R3. A schematic outline describing the assembly of the interferon gene containing ribosome binding sites R2 and R3 is presented in FIG. 3. The original gene construction containing R1 is shown schematically at the top of the figure. By restriction first with HindIII and then AluI, an AluI-HindIII duplex is generated. An EcoRI-AluI duplex containing either R2 or R3 sequences (left part of figure) is then joined to the AluI-HindIII duplex. As indicated in the bottom part of FIG. 3, the total gene is then resynthesized.

The interferon gene with R1 and assembled in pMP105 was cut with EcoRI and HindIII. The 384 base pair EcoRI-HindIII duplex was then cut with AluI. By first cutting the gene with HindIII, the only other AluI recognition site within the gene (HindIII site) was present as single strands and hence inactivated. The 267 base pair AluI-HindIII duplex was isolated and ligated to the EcoRI-AluI duplex containing either R2 or R3. The new EcoRI-HindIII duplexes were then cloned into pUC8, amplified, and reisolated. Finally, each 384 base pair EcoRI-HindIII duplex containing either R2 or R3 was ligated to the remainder of the gene (HindIII-EcoRI) and inserted into pUC8. Plasmids having duplexes with both orientations of the gene with respect to the cloning vehicle could be identified.

EXAMPLE 8

Expression in E. coli and and Biological Activity of α-C Lymphoblastoid Hybrid Interferon The lymphoblastoid hybrid interferon gene was expressed in E. coli as a pUC8 plasmid derivative and found to be biologically active as determined by the cytopathic effect reduction assay. Three different constructions of the gene containing ribosome binding sites R1, R2, and R3 were assayed. Results of various experiments are presented in Tables 13 and 14.

TABLE 13

A Summary of the Lymphoblastoid Hybrid Interferon Assays as Determined by the Cytopathic Reduction Effect[1]

| Gene Control Region | Interferon Yield[2] (mg/l) |
|---|---|
| R1 | 0.3 |
| R1 | 0.15 |
| R1 | 0.15 |
| R2 | 9 |
| R2 | 5 |
| R2 | 2 |
| R3 | 0.2 |
| R3 | 0.2 |
| R3 | 0.2 |

[1]Assay was with a bovine kidney cell line MDBK using vesicular stomatitis virus as challenge.
[2]Cells were assayed at $OD_{578\ nm}$ of 4–5.

TABLE 14

Titration of Lymphoblastoid-Leukocyte α-C Hybrid Interferon Activity Using Three Ribosome Binding Sites (R1, R2, R3)

| E. coli Cell Strain | Ribosome Binding Site | # of Colonies Tested | Mode of Interferon Determination | |
|---|---|---|---|---|
| | | | RIA* | CPE** |
| W3110 | 1 | 3 | 160 μg/l | 70 μg/l |
| | 2 | 3 | 550 μg/l | 350 μg/l |
| | 3 | 3 | 100 μg/l | 60 μg/l |
| 7118 | 1 | 3 | 75 μg/l | 6 μg/l |
| | 2 | 3 | 700 μg/l | 500 μg/l |
| | 3 | 3 | 15 μg/l | 6 μg/l |
| 7902 | 1 | 3 | 50 μg/l | 200 μg/l |
| | 2 | 3 | 2.5 μg/l | 5 μg/l |
| | 3 | 3 | 50 μg/l | 200 μg/l |

*RIA — radioimmune assay using a standard α-interferon antibody.
**CPE — cytopatic effect reduction assay using a bovine kidney cell line (MDBK) and vesicular stomatitis virus as challenge. Specific activity with this assay was $5$–$10 \times 10^8$ units/mg protein.

The hydrid interferon had a specific activity $1$–$1 \times 10^8$ units/mg when assayed on a bovine kidney cell line (MDBK) when challenged with vesicular stomatitis virus. All three ribosome binding sites appear to be translationally active. The order of translation initiation activity is $R2 > R3 \geq R1$.

The levels of expression were evaluated by gel electrophoresis of total cell protein. Cell lysates of strains of E. coli having R1, R2, and R3 controlled genes were assessed. Cell lysate material was obtained for this gel analysis by growing E. coli containing pMP105 to 0.4–0.6 $OD_{578}$ in nutrient media supplemented with ampicillin and incuded with $10^{-3}$M IPTG. After 3 hours, cells were harvested, lysed by sonication and aliquots loaded on gels. The amount of interferon hybrid protein produced by each ribosome binding site is consistent with the results obtained using the virus challenge assay. More interferon appears to be produced from R2 than from either R3 or R1.

EXAMPLE 9

Chemical Synthesis of Oligodeoxynucleotides

Oligodeoxynucleotides containing control region sequences (promoter, lac operator and ribosome binding sites) were synthesized on silica gel polymer supports using 5'-dimethoxytrityldeoxynucleotide-3-tetrazoylphosphoramidites as synthons. All other oligodeoxynucleotides were synthesized similarly on silica gel polymer supports but used 5'-dimethoxytrityldeoxynucleoside-3'-N,N-dimethylaminophosphoramidites as synthons. The chemical procedures have been published [Chemical Synthesis of Oligodeoxynucleotides Using the Phosphite Triester Intermediates. M. H. Caruthers, In Chemical and Enzymatic Synthesis of Gene Fragments. Ed. by H. G. Gasson and Anno Lang. Verlag Chemie, Deerfield Beach, Fla., (1982)]. Upon completion of a synthesis, each oligodeoxynucleotide was freed of protecting groups and isolated by polyacrylamide gel electrophoresis. Silica gel containing the synthetic deoxyoligonucleotide was first treated with triethylammonium thiophenoxide to remove the methyl groups from internucleotide phosphotriesters. The next step was hydrolysis of the ester that joins the oligodeoxynucleotide to the support using concentrated ammonium hydroxide for 3 hours at 20° C. After centrifugation and recovery of the supernatant containing the mixture of failure sequences and the correct oligodeoxynucleotide, the N-benzoyl groups from deoxycytosine and deoxyadenosine and the N-isobutyryl group from deoxyguanosine were removed by warming the concentrated ammonium hydroxide solution at 50° C. for 12 hours. The 5'-O-dimethoxytrityl group was hydrolyzed using 80% acetic acid. The final product was isolated from failure sequences by gel electrophoresis. The hydrolysate was dried in vacuo, dissolved in formamide, warmed at 100° C. for 3 minutes and loaded on to a 12% polyacrylamide gel prepared in 7M urea with a tris-borate buffer (pH 8.0). After gel electrophoresis, oligodeoxynucleotides were visualized on the gel using short wavelength u.v. light with a fluorescent silica gel plate behind the gel. The u.v. absorbing band corresponding to the DNA segment was cut from the gel and the oligodeoxynucleotide eluted. The eluant was extracted four times with n-butanol, dried, redissolved in 0.2 ml water, and freed of salts by column chromatography on a Sephadex G-150/40 column (5 ml syringe) equilibrated with 10 mM triethylammonium bicarbonate (TEAB).

EXAMPLE 10

Preparation of [5'$^{32}$P]-Labelled Oligodeoxynucleotides

Oligodeoxynucleotides (100–500 pmoles) were phosphorylated with T4-polynucleotide kinase and [$\gamma$-$^{32}$P]ATP having a specific activity of 2.5–10$\times$10$^3$ cpm/pmole. The reactions were completed in 5–15 $\mu$l 33 mM Tris-HCl (pH 7.5), 3.3 mM MgCl$_2$ and 5 mM DTT. After 30–40 minutes at 37° C., reaction mixtures were warmed at 75° C. to inactivate T4-kinase. Aliquots were assayed by polyacrylamide gel electrophoresis followed by autoradiography to visualize the results.

EXAMPLE 11

Ligation of Phosphorylated Oligodeoxynucleotides

Reaction mixtures containing 5'-phosphorylated oligodeoxynucleotides (100–500 pmole), [$\gamma$-$^{32}$P]ATP, and inactivated T4-polynucleotide kinase were usually used without purification in ligation reactions. Each pair of complementary sequences was annealed by warming the combined solutions of phosphorylated segments to 95° C. and slowly cooling to 4° C. Two sets of annealed duplexes having a complementary single strand region were then pooled, warmed to 37° C. and cooled slowly to 4° C. The solution was adjusted to 66 mM Tris-HCl (pH 7.5), 6.6 mM MgCl$_2$, 10 mM DTT and 400 $\mu$M ATP in a final volume of 20–30 $\mu$l. After addition of T4-DNA ligase (1–2 units), the reaction mixture was incubated for 12–15 hours and then assayed using polyacrylamide gel electrophoresis. Reaction mixtures were fractionated on Sephadex G-150/40 columns. For ligated DNA segments 40 to 50 nucleotides in length, the column size was 1$\times$20 cm. For larger molecules, the size was 1$\times$90 cm. Before fractionation, each column was washed extensively with 10 mM TEAB and preloaded with 0.5 ml of 95% formamide. The ligation mixture was dried, dissolved in 40 $\mu$l of 95% formamide, warmed for 3 minutes at 100° C., and applied to the column. The DNA was eluted with 10 mM TEAB as 0.2–0.4 ml fractions, collected, and counted. Pooled fractions were dried and redissolved in 10 mM TEAB or a buffer appropriate for the next step.

EXAMPLE 12

Gel Purification

Polyacrylamide gels (8–10%) containing 7M urea were used to isolate completely homogeneous DNA duplexes from ligation mixtures. Routinely, ligation mixtures were dried redissolved in 95% formamide, warmed at 100° C. for 3 minutes and loaded on to the gel. After electrophoresis, the DNA was located by autoradiography and extracted from the gels. The DNA was precipitated from the extract using 2.5 volumes ethanol. After two additional precipitations, the DNA was dried and redissolved in 10 mM TEAB or a buffer appropriate for the next step.

What is claimed is:

1. An antiviral and antiproliferative composition of matter comprising a polypeptide of 166 amino acids and optionally having an additional methionine attached to the ordinary first amino acid at the N-terminus, the amino acid sequence of said polypeptide compound having the formula

$H_2N$[met]-cys$^1$-X-P-Y-B-Z-COOH wherein X consists essentially of amino acids 2 to 46 of human lymphoblastoid interferon (LbIF); Y consists essentially of amino acids 60 to 85 of said LbIF; Z consists essentially of amino acids 112 to 166 of said LbIF; P consists essentially of amino acids 47 to 59 of human $\alpha$C-, $\alpha$F-, or $\alpha$I-type leukocyte interferon (LeIF) and is gln$^{47}$-phe-gln-lys$^{50}$-ala-gln-ala-ileu-ser$^{55}$-val-leu-his-glu$^{59}$, or gln$^{47}$-phe-gln-lys$^{50}$-thr-gln-ala-ileu-ser$^{55}$-val-leu-his-glu$^{59}$; and B consists essentially of amino acids 86 to 111 of human $\alpha$C-, $\alpha$F-, or $\alpha$I-type leukocyte interferon (LeIF) and is ser$^{86}$-thr-glu-leu-tyr$^{90}$-gln-gln-leu-asn-asp$^{95}$-leu-glu-ala-cys-val$^{100}$-ileu-gln-glu-val-gly$^{105}$-val-glu-glu-thr-pro$^{110}$-leu, ser$^{86}$-thr-glu-leu-asn$^{90}$-gln-gln-leu-asn-asp$^{95}$-met-glu-ala-cys-val$^{100}$-ileu-gln-glu-val-gly$^{105}$-val-glu-glu-thr-pro$^{110}$-leu, or ser$^{86}$-thr-glu-leu-tyr$^{90}$-gln-gln-leu-asn-asn$^{95}$-leu-glu-ala-cys-val$^{100}$-ileu-gln-glu-val-gly$^{105}$-met-glu-glu-thr-pro$^{110}$-leu having biological or antiviral activity of human interferon.

2. A hybrid interferon polypeptide according to claim 1 wherein X is a LbIF segment having the amino acid sequence asp$^2$-leu-pro-gln$^5$-thr-his-ser-leu-gly$^{10}$-asn-arg-arg-ala-leu$^{15}$-ileu-leu-leu-ala-gln$^{20}$-met-gly-arg-ileu-ser$^{25}$-leu-phe-ser-cys-leu$^{30}$-lys-asp-arg-his-asp$^{35}$-phe-gly-phe-pro-gln$^{40}$-glu-glu-phe-asp-gly$^{45}$-asn; Y is a LbIF segment having the amino acid sequence met$^{60}$-ileu-gln-gln-ileu-phe$^{65}$-asn-leu-phe-ser-thr$^{70}$-lys-asp-ser-ser-ala$^{75}$-ala-trp-asn-glu-ser$^{80}$-leu-leu-asp-lys-phe$^{85}$; and Z is a LbIF segment having the amino acid sequence met$^{112}$-asn-val-glu$^{115}$-ser-ileu-leu-ala-val$^{120}$-ser-lys-tyr-phe-gln$^{125}$-arg-ileu-thr-leu-tyr$^{130}$-leu-serglu-lys-lys$^{135}$-tyr-ser-pro-cys-ala$^{140}$-trp-glu-ileu-val-arg$^{145}$-ala-glu-ileu-met-arg$^{150}$-ser-leu-thr-leu-leu$^{155}$-thr-asn-leu-gln-glu$^{160}$-arg-leu-arg-asn-lys$^{165}$-asp.

3. A hybrid interferon polypeptide according to claim 2, met-cys$^1$-asp-leu-pro-gln$^5$-thr-his-ser-leu-gly$^{10}$-asn-arg-arg-ala-leu$^{15}$-ileu-leu-leu-ala-gln$^{20}$-met-gly-arg-ileu-ser$^{25}$-leu-phe-ser-cys-leu$^{30}$-lys-asp-arg-his-asp$^{35}$-phe-gly-phe-pro-gln$^{40}$-glu-glu-phe-asp-gly$^{45}$-asn-gln-phe-gln-lys$^{50}$-ala-gln-ala-ileu-ser$^{55}$-val-leu-his-glu-met$^{60}$-ileu-gln-gln-ileu-phe$^{65}$-asn-leu-phe-ser-thr$^{70}$-lys-asp-ser-ser-ala$^{75}$-ala-trp-asn-glu-ser$^{80}$-leu-leu-asp-lys-phe$^{85}$-ser-thr-glu-leu-tyr$^{90}$-gln-gln-leu-asn-asp$^{95}$-leu-glu-ala-cys-val$^{100}$-ileu-gln-glu-val-gly$^{105}$-val-glu-glu-thr-pro$^{110}$-leu-met-asn-val-glu$^{115}$-ser-ileu-leu-leu-ala-val$^{120}$-ser-lys-tyr-phe-gln$^{125}$-arg-ileu-thr-leu-tyr$^{130}$-leu-ser-glu-lys-lys$^{135}$-tyr-ser-pro-cys-ala$^{140}$-trp-glu-ileu-val-arg$^{145}$-ala-glu-ileu-met-arg$^{150}$-ser-leu-thr-leu-leu$^{155}$-thr-asn-leu-gln-glu$^{160}$-arg-leu-arg-asn-lys$^{165}$-asp.

4. A hybrid interferon polypeptide according to claim 2, met-cys$^1$-asp-leu-pro-gln$^5$-thr-his-ser-leu-gly$^{10}$-asn-arg-arg-ala-leu$^{15}$-ileu-leu-leu-ala-gln$^{20}$-met-gly-arg-ileu-ser$^{25}$-leu-phe-ser-cys-leu$^{30}$-lys-asp-arg-his-asp$^{35}$-phe-gly-phe-pro-gln$^{40}$-glu-glu-phe-asp-gly$^{45}$-asn-gln-phe-gln-lys$^{50}$-ala-gln-ala-ileu-ser$^{55}$-val-leu-his-glu-met$^{60}$-ileu-gln-gln-ileu-phe$^{65}$-asn-leu-phe-ser-thr$^{70}$-lys-asp-ser-ser-ala$^{75}$-ala-trp-asn-glu-ser$^{80}$-leu-leu-asp-lys-phe$^{85}$-ser-thr-glu-leu-asn$^{90}$-gln-gln-leu-asn-asp$^{95}$-met-glu-ala-cys-val$^{100}$-ileu-gln-glu-val-gly$^{105}$-val-glu-glu-thr-pro$^{110}$-leu-met-asn-val-glu$^{115}$-ser-ileu-leu-ala-val$^{120}$-ser-lys-tyr-phe-gln$^{125}$arg-ileu-thr-leu-tyr$^{130}$-leu-ser-glu-lys-lys$^{135}$-tyr-ser-pro-cys-ala$^{140}$-trp-glu-ileu-val-arg$^{145}$-ala-glu-ileu-met-arg$^{150}$-ser-leu-thr-leu-leu$^{155}$-thr-asn-leu-gln-glu$^{160}$-arg-leu-arg-asn-lys$^{165}$-asp.

5. A hybrid interferon polypeptide according to claim 2, met-cys$^1$-asp-leu-pro-gln$^5$-thr-his-ser-leu-gly$^{10}$-asn-arg-arg-ala-leu$^{15}$-ileu-leu-leu-ala-gln$^{20}$-met-gly-arg-ileu-ser$^{25}$-leu-phe-ser-cys-leu$^{30}$-lys-asp-arg-his-asp$^{35}$-phe-gly-phe-pro-gln$^{40}$-glu-glu-phe-asp-gly$^{45}$-asn-gln-phe-gln-lys$^{50}$-ala-gln-ala-ileu-ser$^{55}$-val-leu-his-glu-met$^{60}$-ileu-gln-gln-ileu-phe$^{65}$-asn-leu-phe-ser-thr$^{70}$-lys-asp-ser-ser-ala$^{75}$-ala-trp-asn-glu-ser$^{80}$-leu-leu-asp-lys-phe$^{85}$-ser-thr-glu-leu-tyr$^{90}$-gln-gln-leu-asn-asn$^{95}$-leu-glu-ala-cys-val$^{100}$-ileu-gln-asp-val-gly$^{105}$-met-glu-glu-thr-pro$^{110}$-leu-met-asn-val-glu$^{115}$-ser-ileu-leu-ala-val$^{120}$-ser-lys-tyr-phe-gln$^{125}$-arg-ileu-thr-leu-tyr$^{130}$-leu-ser-glu-lys-lys$^{135}$-tyr-ser-pro-cys-ala$^{140}$-trp-glu-ileu-val-arg$^{145}$-ala-glu-ileu-met-rg$^{150}$-ser-leu-thr-leu-leu$^{155}$-thr-asn-leu-gln-glu$^{160}$-arg-leu-arg-asn-lys$^{165}$-asp.

6. A hybrid interferon polypeptide according to claim 2, met-cys$^1$-asp-leu-pro-gln$^5$-thr-his-ser-leu-gly$^{10}$-asn-arg-arg-ala-leu$^{15}$-ileu-leu-leu-ala-gln$^{20}$-met-gly-arg-ileu-ser$^{25}$-leu-phe-ser-cys-leu$^{30}$-lys-asp-arg-his-asp$^{35}$-phe-gly-phe-pro-gln$^{40}$-glu-glu-phe-asp-gly$^{45}$-asn-gln-phe-gln-lys$^{50}$-thr-gln-ala-ileu-ser$^{55}$-val-leu-his-glu-met$^{60}$-ileu-gln-gln-ileu-phe$^{65}$-asn-leu-phe-ser-thr$^{70}$-lys-asp-ser-ser-ala$^{75}$-ala-trp-asn-glu-ser$^{80}$-leu-leu-asp-lys-phe$^{85}$-ser-thr-glu-leu-tyr$^{90}$-gln-gln-leu-asn-asp$^{95}$-leu-glu-ala-cys-val$^{100}$-ileu-gln-glu-val-gly$^{105}$-val-glu-glu-thr-pro$^{110}$-leu-met-asn-val-glu$^{115}$-ser-ileu-leu-ala-val$^{120}$-ser-lys-tyr-phe-gln$^{125}$-arg-ileu-thr-leu-tyr$^{130}$-leu-ser-glu-lys-lys$^{135}$-tyr-ser-pro-cys-ala$^{140}$-trp-glu-ileu-val-arg$^{145}$-ala-glu-ileu-met-arg$^{150}$-ser-leu-thr-leu-leu$^{155}$-thr-asn-leu-gln-glu$^{160}$-arg-leu-arg-asn-lys$^{165}$-asp.

7. A hybrid interferon polypeptide according to claim 2, met-cys$^1$-asp-leu-pro-gln$^5$-thr-his-ser-leu-gly$^{10}$-asn-arg-arg-ala-leu$^{15}$-ileu-leu-leu-ala-gln$^{20}$-met-gly-arg-ileu-ser$^{25}$-leu-phe-ser-cys-leu$^{30}$-lys-asp-arg-his-asp$^{35}$-phe-gly-phe-pro-gln$^{40}$-glu-glu-phe-asp-gly$^{45}$-asn-gln-phe-gln-phe-gln-lys$^{50}$-thr-gln-ala-ileu-ser$^{55}$-val-leu-his-glu-met$^{60}$-ileu-gln-gln-ileu-phe$^{65}$-asn-leu-phe-ser-thr$^{70}$-lys-asp-ser-ser-ala$^{75}$-ala-trp-asn-glu-ser$^{80}$-leu-leu-asp-lys-phe$^{85}$-ser-thr-glu-leu-asn$^{90}$-gln-gln-leu-asn-asp$^{95}$-met-glu-ala-cys-val$^{100}$-ileu-gln-glu-val-gly$^{105}$-val-glu-glu-thr-pro$^{110}$-leu-met-asn-val-glu$^{115}$-ser-ileu-leu-ala-val$^{120}$-ser-lys-tyr-phe-gln$^{125}$-arg-ileu-thr-leu-tyr$^{130}$-leu-ser-glu-lys-lys$^{135}$-tyr-ser-pro-cys-ala$^{140}$-trp-glu-ileu-val-arg$^{145}$-ala-glu-ileu-met-arg$^{150}$-ser-leu-thr-leu-leu$^{155}$-thr-asn-leu-gln-glu$^{160}$-arg-leu-arg-asn-lys$^{165}$-asp.

8. A hybrid interferon polypeptide according to claim 2, met-cys$^1$-asp-leu-pro-gln$^5$-thr-his-ser-leu-gly$^{10}$-asn-arg-arg-ala-leu$^{15}$-ileu-leu-leu-ala-gln$^{20}$-met-gly-arg-ileu-ser$^{25}$-leu-phe-ser-cys-leu$^{30}$-lys-asp-arg-his-asp$^{35}$-phe-gly-phe-pro-gln$^{40}$-glu-glu-phe-asp-gly$^{45}$-asn-gln-phe-gln-lys$^{50}$-thr-gln-ala-ileu-ser$^{55}$-val-leu-his-glu-met$^{60}$-ileu-gln-gln-ileu-phe$^{65}$-asn-leu-phe-ser-thr$^{70}$-lys-asp-ser-ser-ala$^{75}$-ala-trp-asn-glu-ser$^{80}$-leu-leu-asp-lys-phe$^{85}$-ser-thr-glu-leu-tyr$^{90}$-gln-gln-leu-asn-asn$^{95}$-leu-glu-ala-cys-val$^{100}$-ileu-gln-asp-val-gly$^{105}$-met-glu-glu-thr-pro$^{110}$-leu-met-asn-val-glu$^{115}$-ser-ileu-leu-ala-val$^{120}$-ser-lys-tyr-phe-gln$^{125}$-arg-ileu-thr-leu-tyr$^{130}$-leu-ser-glu-lys-lys$^{135}$-tyr-ser-pro-cys-ala$^{140}$-trp-glu-ileu-val-arg$^{145}$-ala-glu-ileu-met-arg$^{150}$-ser-leu-thr-leu-leu$^{155}$-thr-asn-leu-gln-glu$^{160}$-arg-leu-arg-asn-lys$^{165}$-asp.

* * * * *